United States Patent [19]
Kenten et al.

[11] Patent Number: 6,087,476
[45] Date of Patent: Jul. 11, 2000

[54] LUMINESCENT CHIMERIC PROTEINS

[75] Inventors: John H. Kenten, Gaithersburg; Jan Casadei, Bethesda; Michael J. Powell, Gaithersburg, all of Md.

[73] Assignee: IGEN International, Inc., Gaithersburg, Md.

[21] Appl. No.: 08/906,654

[22] Filed: Aug. 7, 1997

Related U.S. Application Data

[63] Continuation of application No. 08/358,577, Dec. 14, 1994, abandoned, which is a continuation of application No. 08/110,326, Aug. 23, 1993, abandoned, which is a continuation of application No. 07/789,279, Nov. 7, 1991, abandoned, which is a continuation of application No. 07/173,231, Mar. 24, 1988, abandoned.

[51] Int. Cl.$^7$ .............................. C07K 14/00; C12N 9/00
[52] U.S. Cl. ........................... 530/350; 530/399; 435/183
[58] Field of Search ................................ 530/350, 387.3, 530/399, 387.2, 391.2; 435/69.7

[56] References Cited

U.S. PATENT DOCUMENTS

| | | |
|---|---|---|
| 4,098,876 | 7/1978 | Piasio et al. . |
| 4,376,110 | 3/1983 | David et al. . |
| 4,412,001 | 10/1983 | Baldwin et al. . |
| 4,536,479 | 8/1985 | Vander-Mallie . |
| 4,581,335 | 4/1986 | Kosak . |
| 4,591,552 | 5/1986 | Neureth . |
| 4,604,364 | 8/1986 | Kosak ..................................... 436/501 |
| 4,614,712 | 9/1986 | Baldwin et al. . |
| 4,665,022 | 5/1987 | Schaeffer et al. . |
| 4,687,747 | 8/1987 | Lin . |
| 4,691,009 | 9/1987 | Palmer ..................................... 530/350 |
| 4,753,873 | 6/1988 | Beltz et al. . |
| 4,816,567 | 3/1989 | Cabilly et al. . |

FOREIGN PATENT DOCUMENTS

| | | |
|---|---|---|
| 0 125 023 | 11/1986 | Anguilla . |
| 0 137 515 | of 0000 | European Pat. Off. . |
| 0 187 519 | of 0000 | European Pat. Off. . |
| 120694 | 10/1984 | European Pat. Off. . |
| 0 184 187 | 6/1986 | European Pat. Off. . |
| 2008247 | 5/1979 | United Kingdom . |
| WO 86/01533 | 3/1986 | WIPO . |
| WO 86/02077 | 4/1986 | WIPO . |
| WO 86/06742 | 11/1986 | WIPO . |
| 8703304 | 6/1987 | WIPO . |
| WO 87/03304 | 6/1987 | WIPO . |
| 87/06707 | 11/1987 | WIPO . |
| 88/00617 | 1/1988 | WIPO . |

OTHER PUBLICATIONS

Pirker et al 1985 Caner Res. 45:751–757 1.
Murphy et al 1986 P.N.A.S. 83:8258–8262.
DeWet et al 1987 Mol. Cell Biol 7(2): 725–737.
Inouye et al 1985 P.N.A.S. 82:3154–3158.
1. Campbell, A. K. et al., *Methods of Biochemical Analysis* 31: 317–416, J. Wiley & Sons, Inc., London (1985) (Cited on pp. 2 and 3 of the application).
2. Neuberger, M. S., et al. *Nature* 312: 604–612 (1984) (Cited on pp. 3 and 17 of the application).
3. Neuberger, M. S., *Trends in Biochemical Science*, 347–349 (1985) (Cited on p. 3 of the application).
4. Morrison, *Science 229*: 1202 (1985) (Cited on p. 3 of the application).
7. Sharon, J., et al., *Nature 309*: 54 (1984) (Cited on p. 3 of the application).
8. Oi and Morrison, *Biotechniques 4*: 214 (1986) (Cited on p. 4 of the application).
12. Inouye et al., *P.N.A.S. 82*: 3154–3158 (1985) (Cited on pp. 4 and 36 of the application).
14. Inouye et al., *Biochem. 25*: 8425–8429 (1986) (Cited on pp. 4 and 39 of the application).
15. Tsuji, F.T., et al., *P.N.A.S. (USA) 83*: 8107–8111 (1986) (Cited on p. 5 of the application).
16. Vora, S., *Analytical Biochem. 144*: 307–318 (Cited on p. 5 of the application).
17. Schwartz, E.F., et al., *Biochem. Biophys. Res. Commun. 35*: 115–120 (1969) (Cited p. 12 of the application).
18. Stollar, B.D., et al., *Virol. 42*: 276–280 (1970) (Cited on p. 12 of the application).
19. Talal, N., et al., *Nature New Biol. 240*: 240–242 (1970) (Cited on p. 12 of the application).
20. Stollar, B.D., *Science 169*: 609–611 (1970) (Cited on p. 12 of the application).
21. Matre, R.J., *J. of Immunol. Met. 5*: 345–352 (1974) (Cited on p. 12 of the application).
22. De Zoeten, G.A., et al., *Virol. 70*: 459–469 (1976) (Cited on p. 12 of the application).
23. Stumph, W.E., et al., *J. Cell. Biol. 75*: 127(a) (1977) (Cited on p. 12 of the application).
24. Pesce, A.J., et al., *Clin. Chem. 20*: 253–259 (1974) (Cited on p. 12 of the application).
25. DeLange, H., *J. Bio. Chem. 246*: 698 (1971) (Cited on p. 12 of the application).
27. *Textbook of Clinical Chemistry*, N. W., Ed., W.B. Saunders Co., Philadelphia, Pennsylvania, pp. 1000–1003 (Cited on p. 14 of the application).
28. Lincoln et al., *Rec. Prog. Horm. Res. 36*: 1 (1980) (Cited on p. 14 of the application).
29. Nakao, K., et al., *Biochim. Biophys. Res. Commun.*, 124: 815 (1984) (Cited on p. 14 of the application).
30. Dzau, V.J., et al., *Clin. Exp. Hypertens.*, A5(7&8): 1207 (1983) (Cited on p. 14 of the application).
31. Tanaka, I., et al., *Biochim., Biophys. Res. Commun.*, 124: 663 (1984) (Cited on p. 14 of the application).
33. Dreesman, G.R., et al., *Nature 295*: 158–160 (1982) (Cited on p. 14 of the application).

(List continued on next page.)

*Primary Examiner*—Karen Cochrane Carlson
*Attorney, Agent, or Firm*—Whitman Breed Abbott & Morgan LLP

[57] ABSTRACT

The invention relates to luminescent chimeric proteins which include a photoprotein and a second protein which may be light- or heavy-chain immunoglobulin, an antigenic peptide, avidin, streptavidin, or protein A. The invention also relates to chimeric protein genes, plasmids containing said gene, and hosts transformed with said plasmid. The invention also relates to a range of highly sensitive immunoassays which use the chimeric proteins.

5 Claims, 9 Drawing Sheets

OTHER PUBLICATIONS

34. Gnann, Jr., J.W., et al., *Science 237*: 1346–1349 (1987) (Cited on pp. 15 and 46 of the application).
35. Prasher. D. et al., *Biochim. Biophys. Res. Commun. 126 3*: 1259–1268 (Cited on pp. 15, 34 and 37 of the application).
36. Hori, K., et al., *Biochemistry 14*: 2371–2376 (1975) (Cited on p. 15 of the application).
37. Hori, K., et al., *P.N.A.S. (USA) 74*: 4285–4287 (1977) (Cited on pp. 15 and 38 of the application).
38. Inoue, S., et al., *Chem. Lett.* 141–144 (1975) (Cited on p. 15 of the application).
39. Faust, C.H., et al., *Biochim. 18*: 1106–1119 (1979) (Cited on pp. 16, 34 of the application).
40. Gubler, U., et al., *Gene 25*: 263–269 (1983) (Cited on p. 16 of the application).
41 De Wet, J.R., et al., *P.N.A.S. (USA) 82*: 7870–7873 (1985) (Cited on p. 16 of the application).
42. Huhynh T.V., et al., *DNA Cloning—A Practical Approach 1*: 49–78, Glover (Ed), IRL Press, Washington, D.C. (Cited on pp. 16, and 35 of the application).
43. Linscott's *Directory of Immunological and Biological Reagents*, 4th Ed., 1–23 (1986–1987) (Cited on p. 17 of the application).
44. Okayama, H., *Mol. Cell Biol. 3*: 280 (1983) (Cited on p. 18 of the application).
45. Diamond et al., *N. Eng. J. Med. 304*: 1344 (1981) (Cited on p. 20 of the application).
46. Kennett, McKearn and Bechtol (eds.), *Monoclonal Antibodies: Hybridomas—A new Dimension in Biologic Analysis*, Plenum, 1980 (Cited on p. 20 of the application).
47. Banerji, J., et al., *Cell 33*: 729–740 (1983) (Cited on p. 20 of the application).
48. Potter, H., et al., *P.N.A.S. (USA) 81*: 7161–7165 (1984) (Cited on p. 20 of the application).
51. Johnson, F.G., et al., *Methods in Enzymol.* 57: 271–291 (1978) (Cited on p. 33 of the application).
52. Kenten, J.H., et al., *P.N.A.S. (USA) 79*: 6661–6665 (1982) (Cited on p. 35 of the.
53.
54. Benton, W.D., et al., *Science 196*: 180–182 (1977) (Cited on p. 35 of the application).
55. Maniatis, T., et al., *Molecular Cloning (A Laboratory Manula)*, Cold Spring Harbor Laboratory (1982) (Cited on pp. 35, 36 and 37 of the application).
56. Norrander, J., et al., *Gene 26*: 101–106 (1983) (Cited on p. 37 of the application).
57. Oi et al., *P.N.A.S. (USA) 80*: 825–829 (1983) (Cited on p. 41 of the application).
58. Coffino, P., et al., *P.N.A.S. (USA) 68*: 219–223 (1971) (Cited on p. 41 of the application).
59. Laemmli, U.K., *Nature (London) 227*: 680–685 (1970) (Cited on p. 42 of the application).
60. Neuberger, M.S., *EMBO J 2*: 1373–1378 (1983) (Cited on p. 43 of the application).
61. Bothwell, A.L.M., et al., *Cell 24*: 625–637 (1981) (Cited on p. 43 of the application).
62. Newell, N., et al., *Science 209*: 1128–1132 (1980) (Cited on p. 43 of the application).
63. Sakono, H., et al., *Nature 286*: 676–683 (1980) (Cited on p. 43 of the application).
64. Early, P., et al., *Cell 19*: 981–992 (1980) (Cited on p. 43 of the application).
65. Kim, S., et al., *Cell 27*: 573–581 (1981) (Cited on p. 43 of the application).
66. Gough, N.M., et al., *P.N.A.S. (USA) 78*: 509–513 (1981) (Cited on p. 43 of the application).
67. Gillies, S.D., et al., *Cell 33*: 717–728 (1983) (Cited on p. 43 of the application).
68. Gilliam, A.C. et al., *P.N.A.S. (USA) 81*: 4164–4168 (1984) (Cited on p. 43 of the application).
69. Takahashi, N., et al., *Gene 11*: 117–127 (1980) (Cited on p. 43 of the application).
70. Yamawaki–Kataoka, Y., et al, *Nature 283*: 786–789 (1982) (Cited on p. 43 of the application).
71. Tucker, P.N. et. al., *Science 206*: 1299–1303 (1979) (Cited on p. 43 of the application).
72. Ollo, R., et al., *Nature 296*: 761–763 (1982) (Cited on p. 43 of the application).
73. Kataoka, T., et al., *P.N.A.S. (USA) 76*: 4240–4244 (1979) (Cited on p. 43 of the application).
74. Zakut, R., et al., *Nucl. Acid Res. 8*: 453–466 (1980) (Cited on p. 43 of the application).
75. Moussebois et al., *J.I.M. 54*: 159–164 (1982) (Cited on pp. 50 and 53 of the application).
76. McElroy, D.R., PCT Patent Application 87/03304 (Pub. Apr. 6, 1987).
79. De Wet, J.R., *Mol. and Cell Bio. 7*: 725–737 (1987).
80. Prasher, D.C., *Biochem. 26*: 1326–1332 ((1987).
81. Noguchi, M. *Methods of Enzym. 133*: 298–306 (1986).
82. Prasher, D.C. *Methods of Enzym. 133*: 288–298 (1986).
83. Cormier, J.L et al., *Bioluminescence: Recent Advances* pp. 255–271 (1975).
84. Shimomura, O. et al., *Nature 227*: 1356–1357 (1970).
85. Shimomura, O. et al., *P.N.A.S. 75* 2611–2615 (1978).
86. *British Science News 196*/1 p. 5 (1986).
87. Morin, J.G. et al., *J. Cell Physiol. 77*: 305–311.
88. McElroy, W.D., DeLuca, M.A., *J. Appl. Biochem. 5*: 187–209 (1983).
89. Campbell, A.K. et al., *Techniques in the Life Sciences*, B2/II, pp. B213/1–B213–56.
90. Campbell, A.K., *Trends in Biochemical Sciences 11*: 1–5.
91. Engebrecht, J. et al., *Cell 32*: 773–781 (1983).
92. Cohn et al., *P.N.A.S. (U.S.A.) 80*: 120–123 (1983).
94. Sun, L.K. et al., *P.N.A.S. 84*: 214–218 (1987).
105. Baldwin et al., Biochem, 23, 3663–67, 1984.
Belas, R., et al., *Bacterial Bioluminescence: Isolation and Expression of the Luciferase Genes form Vibro harveyi*, Science, 218, 791–793, (1982).
Borrelli, E., et al., *Adenovirus–2 E1A Products Repress Enhancer–Induced Stimulation of Transcription*.
Boulianne, G. L., et al. *Production of Functional Chimaeric Mouse/Human Anitbody*, Nature, 312, 643–646, (1984).
Byers, C., et al., *Expression of Bioluminescence by Escherichia coli Containing Recombinant Vibrio harveyi DNA*, Journal of Bacteriology, 169, 247–253, (1987).
Campbell, A.K., et al., *Chemiluminescence Energy Transfer: A Technique for Homogenous Immunoassay*, Chapter 10, 153–183, (1985).
Cormier, M., et al., Renilla and Aequorea Bioluminescence, (1975).
Dzau, V.J., et al., *Antibodies as Specific Renin Inhibitors: Studies with Polyclonal and Monoclonal Antibodies and Fab Fragments*, Clin. and Exper. Hyper.–Theory and Practice, A5(7&8), 1207–1220 (1983).
DeWet, J., et al., *Cloning Firefly Luciferase*, Methods in Enzymology, 133, 3–13, (1986).
Durfor, C., et al., *Antibody Catalysis in Reverse Micelles*, American Chemical Society, 8713–8714 (1988).

Engebrecht, J., et al., *Techniques for Cloning and Analyzing Bioluminescence Genes from Marine Bacteria*, The Agouron Institute, 1–20.

Gupta, S., et al., *Mobilization of Cloned Luciferase Genes into Vibrio harveyi Luminescence mutants*, Arch Microbiol, 143:32–329 (1986).

Margo, G., et al., *Luciferase Genes Cloned from the Unculturable Luminous Bacteriod Symbiont of the Caribbean Flashlight Fish, Krypotophanaron alfredi*, 45:203–209 (1986).

Koncz, C., et al., *Expression and Assembly of Functional Bacterial Luciferase in Plants*, 84, 131–135 (1987).

Jencks, W., et al., *Strain, Distortion, and Conformation Change*, Bio. Chem., 235, 282–320 (1960).

Jones, P., et al., *Replacing the Complementarity–determining regions in a human anitbody with those from a Mouse*, Nature, 321:522–525 (1986).

Kwan, S., et al., *Production of Monoclonal Antibodies*, Genetic Engineering 2:31–46 (1980).

Lerner, R., et al., *Antibodies of Predetermined Specificity in Biology and Medicine*, 36:1–39 ().

Matthews, S., et al., *Living Light—From Ocean to Hospital Bed*, Spectrum, 196:5–7 (1986).

Morrison, S., et al., *Chimeric Human Antibody Molecules: Mouse Antigen–Binding Domains with human Constant Region Domains*, Proc. Natl. Acad. Sci., 81:6851–6855 (1984).

Mulligan, R., et al., *Selection for Animal Cells that Express the Escheichia coli gene coding for Xanthine–Guanine Phosphoribosyltransferase*, Proc. Natl. Acad. Sci. 78:2072–2076 (1981).

Neuberger, M., et al., Recombinant Antibodies Possessing Novel Effector Functions.

Neuberger, M., et al., *Expression and Regulation of Immunoglobulin Heavy Chain Gene Transfected into Lymphoid Cells*, EMBO Journal 2:1373–1378 (1983).

Neuberger, M., et al., *Switch from Hapten–Specific Immunoglobin M to immunoglobulin D Secretion in a Hybrid Mouse Cell Line*, Proc. Natl. Acad. Sci., 78:1135–1142 (1981).

Neuberger, M., et al., *A Hapten–Specific Chimaeric IgE Antibody with Human Physiological Effector Function*, Nature, 314:268–270 (1985).

Noguchi, M., et al., Molecular Cloning of Apoaequorin cDNA, Methods in Enzymology, 133:298–306 (1986).

Marx, J., et al., *Antibodies Made to Order: Chimeric Antibodies—Which are part Mouse and part Human—May Help Solve the Problems Hindering the theraputic Use of Monoclonal Antibodies*, Science, 229:455–456 (1985).

Prasher, D., et al., *Isolation and Expression of cDNA Coding for Aequorin, the $CA^{2+}$–Activated Photoprotein from Aequorea Victoria*, Methods in Enzymology, 133:288–297 (1986).

Prasher, D., et al., *Cloning and Expression of the cDNA Coding for Aequorin, A Bioluminescent Calcium–Binding Protein*, Biochemical and Biophysical Research Communications, 126:1259–1268 (1985).

Ow, D., et al., *Transient and Stable Expression of the Firefly Luciferase Gene in Plant Cells and Transgenic Plants*, Science, 234:856–859 (1986).

Pollack, S., et al., *Selective Chemical Catalysis by an Antibody*, Science, 234:1570–1573 (1986).

Royer, G., et al., *Enzyme–like Synthetic Catalysts (Synzymes)*, 197–227.

Shaw, J., et al., *Development of A Vibrio Bioluminescence Gene–Set To Monitor Phytopathogenic Bacteria During the Ongoing Disease Process in a Non–Disruptive Manner*, BioTechnology, 4:560–564 (1986).

Sharon, J., et al., *Expression of $V_H C^K$ Chimaeric Protein in Mouse Myeloma Cells*, Nature, 309.

Shimomura, O., et al., *Properties of the Bioluminescent Protein Aequorin*, Biochemistry, 8:3991–3997 (1989).

Tramontano, A., et al., Catalytic Antibodies, Science, 234:1566–1573 (1986).

Ward, W., et al., *Properties of Mnemiopsin and Berovin, Calcium–Activated Photoproteins from the Ctenophores Mnemiopsis sp. and Beroe ovata*, Biochemistry, 13:1500–1510 (1974).

Ward, W., et al., Extraction and Purification of Calcium–Activated Photoproteins from the Ctenophores Mnemiopsis sp. and Beroe ovata, Biochemistry, 13:1491–1499 (1974).

Ward, W., et al., *General Aspects of Bioluminescence*, Biochemistry, 321–358 (.

Williams, G., et al., Production of Antibody–tagged Enzymes by Myeloma Cells: Application of DNA Polymerase I Klenow Fragment, Gene, 43:319–324 (1986).

Wood, K., et al., *Photographic Detection of Luminescence in Escherichia coli Containing the Gene for Firefly Luciferase*, Analytical Biochemistry, 161:501–507 (1987).

LUMINESCENT CHIMERIC PROTEINS

CROSS REFERENCES TO RELATED APPLICATIONS

This application is a continuation of U.S. Ser. No. 08/358,577, now abandoned, filed Dec. 14, 1994, which is a continuation of U.S. Ser. No. 08/110,326, now abandoned, filed Aug. 23, 1993 as a continuation of U.S. Ser. No. 07/789,279, now abandoned, filed Nov. 7, 1991 as a continuation of U.S. Ser. No. 07/173,231, now abandoned, filed Mar. 24, 1988.

FIELD OF THE INVENTION

The invention relates to chimeric proteins obtained by genetic engineering. Such chimeric proteins comprise a continuous polypeptide sequence in which a photoprotein is linked to an antigenically active protein or fraction thereof. The invention also relates to chimeric antibodies in which the $F_c$ portion has been replaced with a photoprotein to comprise a continuous polypeptide sequence. The invention further relates to chimeric proteins which comprise a continuous polypeptide sequence in which a photoprotein is linked to a protein with specific affinities, such as avidin, streptavidin, or protein A. The invention relates as well to the cloning and production of these chimeric proteins and to methods of using these proteins in immunodiagnostic or imaging processes.

BACKGROUND OF THE INVENTION

The luminescent protein aequorin originates from the circumoral ring of the hydromedusa *Aequorea victoria*. When aequorin is bound to luciferin, it emits light on addition of $Ca^{++}$. The binding of $Ca^{++}$ to the aequorin-luciferin complex causes oxidation of the bound luciferin (an imidazopyrazine) yielding light (lambda max=470 nm) and carbon dioxide. This rapid oxidation allows for the detection of amols ($10^{-18}$) of photoprotein (Campbell, A. K., et al., *Methods of Biochemical Analysis* 31:317–416, J. Wiley & Sons, Inc., London (1985)). The ability to detect this protein (and other proteins such as luciferase) at low concentrations, and its utility in a number of assays (Campbell, A. K., et al., *Methods of Biochemical Analysis*, 31:317–416, J. Wiley & Sons, Inc., London (1985)), suggests that a chimeric protein possessing specific affinity for analytes of interest as a chimeric protein possessing epitopes of an analyte (either immunoglobulins or antigens or portions thereof), and incorporating a photoprotein, would be of great value in immunoassay systems.

A chimeric gene is one comprising DNA or RNA genetic sequences from more than one source. The continuous polypeptide sequence or protein resulting from the expression of a chimeric genetic sequence is referred to here as a chimeric protein. A chimeric immunoglobulin is an immunoglobulin in which one or more of the subchains is a chimeric protein.

Chimeric immunoglobulins have been produced by the standard methods of genetic engineering. They may contain as an integral part of their structure enzymes and other biologically active peptides. Neuberger, M. S., et al., *Nature* 312:604–612 (1984); Neuberger, M. S., *Trends in Biochemical Science*, 347–349 (1985), Morrison, *Science* 229:1202 (1985). Chimeric antibodies have been produced which incorporate protein toxins, such as ricin, for selective destruction of specific target cells. PCT Patent Application PCT/GB85/00392, European Patent Application 120,694. Chimeric immunoglobulins have also been constructed which contain, as the incorporated genetic sequence, a section of another immunoglobulin gene from the same species. Sharon, J., et al., *Nature* 309:54 (1984). Immunoglobulin genetic sequences originating in different species have also been created and expressed as protein product. Oi and Morrison, *Biotechniques* 4:214 (1986). However, no immunoglobulin incorporating a photoprotein as an integral part of a chimeric protein structure is disclosed by the prior art.

Immunoglobulins tagged with photoproteins by conventional, i.e., nongenetic, biochemical linking methods have the utility of antibodies labeled with light emitting compounds and provide a sensitive and specific method of detecting an analyte of interest. U.K. Patent Application GB/2008247, European Patent Application 0137 515, U.S. Pat. No. 4,604,364. While immunoglobulins so tagged have proved useful, conventional methods of attaching photoproteins to immunoglobulins and antigens are difficult to perform and often lead to inactivation of the protein. Steric interference caused by the fused protein may also interfere with the proper binding of the immunoglobulin.

The genetic sequence of aequorin photoprotein is known (Inouye et al., *Proc. Nat. Acad. Sci.* 82:3154–3158 (1985)) and techniques have been disclosed to obtain the aequorin genetic sequence in a cloning vector (European Patent Application 0 187 519, Inouye et al., *Biochem.* 25:8425–8429 (1986)). It could not be predicted, however, whether a chimeric protein created by these techniques and containing aequorin would have the desirable luminescent properties of aequorin or any specific and desirable property of the immunoglobulin.

Both immunoglobulins and photoproteins depend for their proper functioning on their 3-dimensional structure. Such a 3-dimensional (tertiary) structure is frequently sensitive to and disrupted by changes in amino acid sequence (Tsuji, F. T., et al., *Proc. Nat'l Acad. Sci. U.S.A.* 83:8107–8111 (1986)). It could not be expected that the insertion of a genetic sequence for a photoprotein into the midst of the sequence of an immunoglobulin chain would produce a chimeric immunoglobulin which would properly function as desired. Similarly, in other chimeric photoproteins, such as chimeric photoprotein-antigens, changes in 3-dimensional folding in the chimeric protein could interfere or modify the properties of the chimeric protein in unexpected ways. Vora, S., *Analytical Biochem.* 144:307–318.

SUMMARY OF THE INVENTION

The invention broadly relates to a DNA or RNA genetic sequence encoding for a continuous polypeptide sequence which contains a photoprotein and a second protein, said DNA or RNA genetic sequence containing (a) a DNA or RNA sequence encoding for a photoprotein, and (b) a DNA or RNA sequence encoding for a second protein selected from the group consisting of light- or heavy-chain immunoglobulin, an antigenic peptide or fragment thereof, avidin, streptavidin, or protein A. The genetic sequence is capable of expressing a continuous polypeptide sequence wherein the second protein is bound to the photoprotein at the C- or N- terminus. In another embodiment, the DNA or RNA genetic sequence is one which encodes for a member of the group consisting of a heavy-chain immunoglobulin, an antigenic peptide or fragment thereof, avidin, streptavidin, and protein A, a portion of which member has been substituted by a photoprotein. A related embodiment includes a DNA or RNA genetic sequence which encodes for an antigen-specific, chimeric, bifunctional, continuous polypeptide sequence derived from a heavy-chain immunoglobulin specific to an antigen, a portion of the genetic sequence having been replaced with the sequence encoding for a photoprotein. In still a further embodiment, the DNA or RNA genetic sequence encoding for an antigen-specific continuous polypeptide sequence is one wherein the DNA or RNA genetic sequence comprises (a) a DNA or RNA sequence encoding for a remnant of an antigen-specific immunoglobulin, which remnant comprises the $V_H$ and CH-1 domain of said immunoglobulin, and (b) a DNA or RNA sequence which encodes for a photoprotein.

The invention also encompasses cloning and expression vectors containing the genetic sequences which code for the chimeric protein molecules, host cells transformed with such vectors, and methods for producing such chimeric molecules by expression of the underlying genetic sequence in such hosts.

The invention is also directed to chimeric proteins which comprise a continuous polypeptide sequence and which contain (a) a photoprotein, and (b) a second protein selected from the group consisting of a light- or heavy-chain immunoglobulin, an antigenic peptide, avidin, streptavidin, or protein A. The second protein is bound to the first protein at the C- or N- terminus. In a preferred embodiment, the chimeric protein comprises a continuous polypeptide sequence which contains a member of the group consisting of heavy-chain immunoglobulin, an antigenic peptide, avidin, streptavidin, and protein A, a portion of which member has been substituted by a photoprotein.

The invention further encompasses immunodiagnostic assays which employ the chimeric proteins of the invention. Such assays include sandwich immunoassays, competition immunoassays, simultaneous immunoassays, reverse immunoassays, forward immunoassays, and other homogeneous and heterogeneous assays as known in the art. Broadly, the assays are for the detection of an analyte of interest and comprise the steps of contacting a chimeric protein which has binding specificity for an analyte of interest with a sample containing the analyte of interest and forming thereby a chimeric protein-analyte of interest complex. The photoprotein portion of that complex is then caused to luminesce, typically by contacting it with luciferin and a source of calcium ion. The luminescence is detected and the presence of the analyte of interest can be determined by measurements relating to the luminescence detected.

In a preferred embodiment, the present invention encompasses a method of detecting HIV-specific antibodies in a sample, comprising the steps of: (a) contacting a sample suspected of containing HIV-specific antibodies with a chimeric protein comprising a continuous polypeptide sequence including both a photoprotein and an HIV diagnostic peptide or fragment thereof, and (b) detecting whether a complex has formed. Since photoproteins may be detected on the level of amols ($10^{-18}$), the immunoassays of the present invention are far more sensitive than traditional enzyme labels. The methods of the invention allow production of intact and functional antibodies which contain an active photoprotein as an integral component of a continuous polypeptide sequence. The use of crosslinking agents to attach the photoprotein to the antibody as described in the prior art, which often results in irreproducible results and loss of activity, is avoided.

DETAILED DESCRIPTION OF THE INVENTION

Introduction

The chimeric proteins of the invention may be used to detect antibodies, antigens, or other specifically binding proteins. The substance which any particular chimeric protein of the invention is designed to detect is referred to as the "analyte of interest."

Antibodies are produced in mammals by lymphocytes known as B cells. The basis for the diversity of antibody specificity for antigens is the presence of variable regions on the genetic sequences coding for both the heavy and light subchains. These variable regions are so-called because during the cell divisions of embryo development these regions are reshuffled by a process known as somatic cell recombination. They are important because they code for the antigen binding sites at the N-terminal sections of immunoglobulin subchains. Genetic sequences containing these variable regions therefore are the key sequences to be included in any chimeric antibody construct.

The invention is broadly directed to a chimeric protein constructed as a continuous polypeptide sequence and comprised of a photoprotein and a second protein. The photoprotein is a protein having fluorescent or luminescent properties and is typically chosen from a class of compounds known as luciferases. Luciferases are enzymes which catalyze the oxidation of the pigment luciferin and thereby induce luminescence. More specifically, the invention is directed to chimeric proteins wherein the photoprotein is a luciferase such as aequorin, obelin, mnemiopsin, or berovin. The invention is also directed to the cloning and production of these novel chimeric proteins.

The second protein is selected from the group consisting of light- or heavy-chain immunoglobulins, an antigenic peptide or antigenically active fragment thereof, avidin, streptavidin, and protein A. Desirably the second protein is an antigenic peptide comprising one or more epitopes or antigenic determinants.

Figure 8:
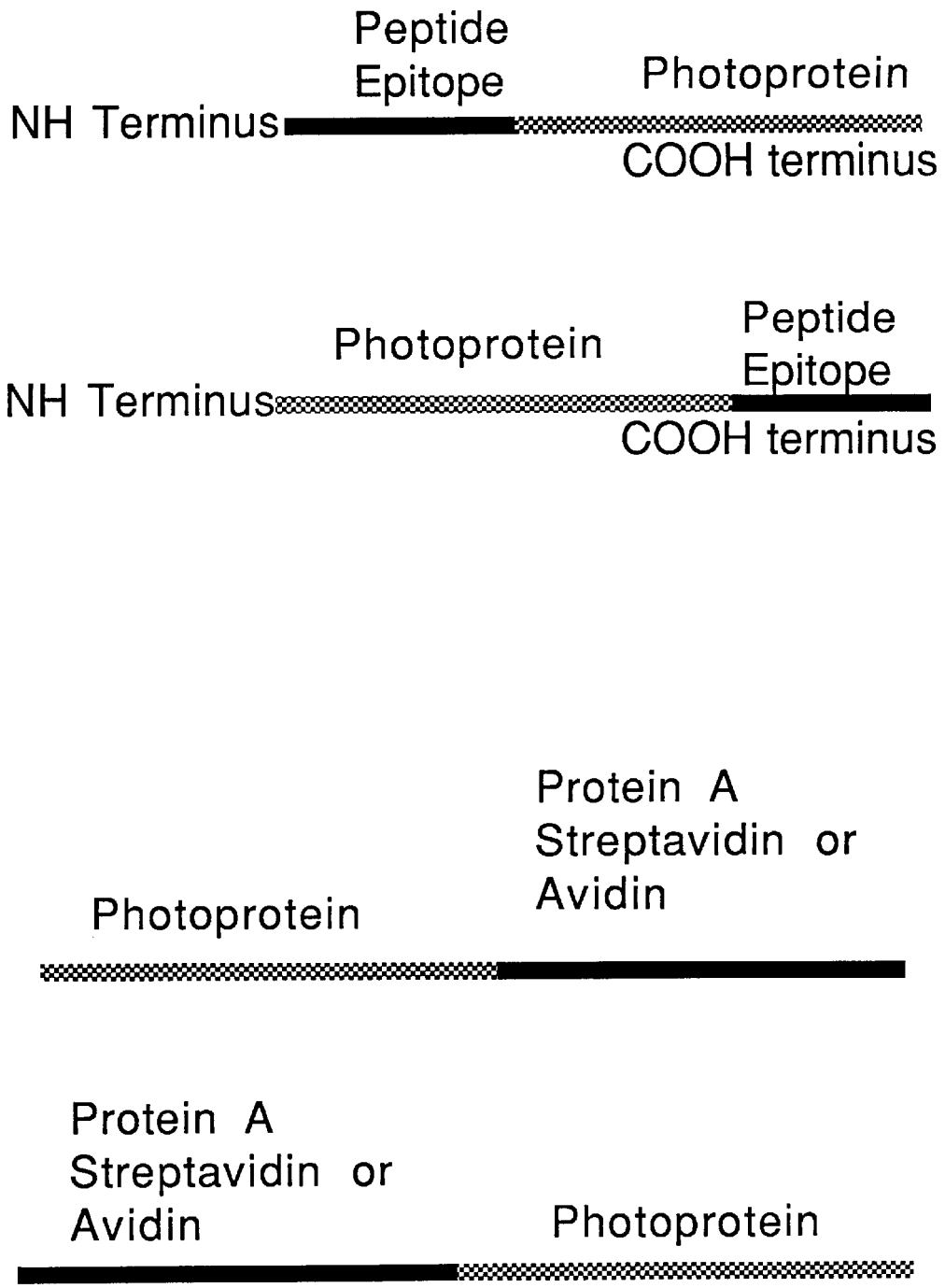
FIG. 8 is a schematic representation of the chimeric proteins of the invention.
Figure 9:
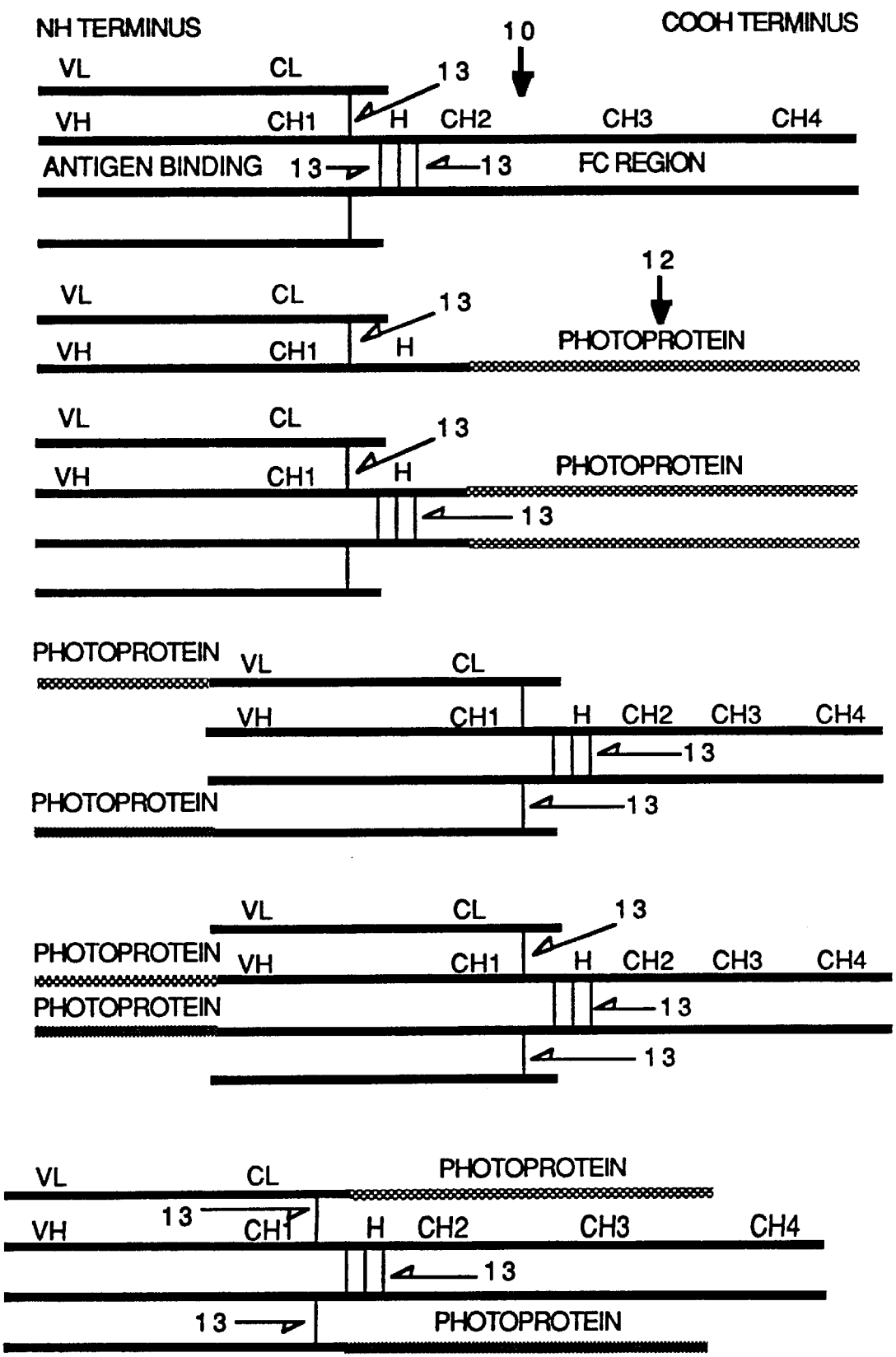
FIG. 9 is a schematic representation of several embodiments of the chimeric proteins of the invention.

The invention may be further understood with reference to FIGS. 8 and 9. FIG. 8 schematically represents chimeric proteins of the invention including photoproteins linked at the N- or C- terminus to the peptide epitope. FIG. 8 also schematically represents the chimeric proteins of the invention which comprise a photoprotein and streptavidin, avidin, or protein A. FIG. 9 is a schematic representation of an immunoglobulin and several examples of antibodies fused with photoproteins in accordance with the invention. Reference numeral 10 on FIG. 9 refers generally to an antibody. Antibodies are tetrameric oligomers consisting of two identical light (L) chains and two identical heavy (H) chains. Each protein chain consists of two principal regions: the N-terminal variable (V) region and the C-terminal constant (C) region. The variable light ($V_L$) and heavy ($V_H$) chains form the variable region domain. The variable domain determines recognition and specificity to a particular antigen. The constant region domains of light ($C_L$) and heavy ($C_H$) chains mediate the effector function responsible for executing the immune response. The hinge region (H) of the antibody molecule connects the $F_{ab}$ fragment to the $F_c$ fragment of the antibody. Reference numeral 12 refers to a chimeric immunoglobulin or protein of the invention wherein a photoprotein has been fused to the heavy chain of an immunoglobulin. Reference numerals 13 refer to disulfide bridges between the several polypeptide sequences shown.

The term chimeric protein as used herein denotes a single polypeptide sequence comprising a photoprotein linked at the N- or C-terminus to a second protein sequence. This second protein sequence may comprise an immunoglobulin light or heavy chain or an antigenic peptide. When expressed in a mammalian cell, the chimeric photoprotein-immunoglobulin chain associates with other light or heavy chains secreted by the cell to provide an antigen-binding antibody. Such a chimeric antibody may contain one or more chimeric immunoglobulin subchains.

The term chimeric immunoglobulin refers to the preferred embodiment in which the $F_c$ portion of one or more heavy subchains has been replaced with a photoprotein such as one of those described above. The $F_c$ region of the antibody structure is at the opposite end of the immunoglobulin heavy chain, towards the C-terminal. It is not involved in antibody recognition, and so is an ideal site for insertion of the photoprotein. The immunoglobulins may be of any immunoglobulin class. The chimeric antibody may, for example, contain a variable region which is specific for hepatitis B surface antigen. As further described below, such antibodies may be used in assays for hepatitis infection according to the methods of the invention.

The chimeric protein of the invention may also be characterized as an antigen-specific chimeric protein comprising a continuous polypeptide sequence, the sequence containing (a) a remnant of an antigen-specific immunoglobulin comprising the $V_H$ and CH-1 domain thereof and (b) a photoprotein.

The chimeric protein may also comprise an antibody capable of binding to DNA, RNA or DNA-RNA hybrids. Antibodies which bind to DNA-RNA hybrids are taught, for example, by Schwartz, E. F., et al., *Biochem. Biophys. Res. Commun.* 35:115–120 (1969); Stollar, B. D., et al., *Virol.* 42:276–280 (1970); Talal, N., et al., *Nature New Biol.* 240:240–242 (1970); Stollar, B. D., *Science* 169:609–611 (1970); Matre, R. J., *J. of Immunol. Met.* 5:345–352 (1974); De Zoeten, G. A., et al., *Virol.* 70:459–469 (1976); Stumph, W. E., et al., *J. Cell. Biol.* 75:127(a) (1977); and Pesce, A. J., et al., *Clin. Chem.* 20:253–259 (1974).

In another embodiment of the invention, the chimeric protein may comprise a photoprotein linked at the N- or C-terminus with avidin, streptavidin, or protein A. This chimeric protein may be used to detect biotinylated DNA or RNA probes or other biotinylated molecules. The amino acid sequence of avidin is taught, for example, by DeLange, H., *J. Bio. Chem.* 246:698 (1971). Methods for cloning streptavidin are taught, for example, by Meade, H. M., et al., PCT Application, Publication No. WO86/02077.

In yet a further embodiment of the invention, the chimeric protein comprises a photoprotein wherein an antigenic peptide is fused at the C- or N-terminus of the photoprotein. Such an antigenic peptide contains at least one epitope which binds immunospecifically with an antianalyte antibody. The peptide may be an analyte-like peptide or may comprise the immunologically reactive epitope of the analyte. A chimeric protein containing an antigenically active peptide is useful for detecting endogenous antibodies as analytes of interest and also for the detection of the antigenically active protein/peptide.

Antigenic peptides for which the invention is applicable include, but are not limited to, polypeptide hormones, including atrial natriuretic factor, angiotensin-II, renin, growth hormone, insulin, glucagon, parathyroid hormone, thyroid stimulating hormone, follicle stimulating hormone, human chorionic gonadotropin (hCG) or choriogonadotropin, thyrotropin-releasing hormone (TRH), gonadotropin-releasing hormone (GnRH) or LH-releasing hormone (LHRH), corticotropin-releasing hormone (CRH), growth hormone-releasing hormone (GHRH), somastatin (SS) or growth hormone-inhibiting hormone (GHIH), thyrotropin or thyroid-stimulating hormone (TSH), follicle-stimulating hormone (FSH), luteinizing hormone (LH), prolactin (PRL), growth hormone (GH) or somatotropin, β-lipotropin (β-LPH), corticotropin or adenocorticotropin (ACTH), β-endorphin (β-END), α-melancycle stimulating hormone (α-MSH), leu-enkephalin (LEK) and met-enkephalin (MEK), vasopressin or antidiuretic hormone (ADH), oxytocin, parathyroid hormone (PTH) or parathormone, relaxin, inhibin, insulin, glucagon, pancreatic polypeptide, gastrin, secretin, cholecystokinin-pancreozymin (CCK-PZ), motilin, vasoactive intestinal peptide (VIP), gastric inhibitory polypeptide (GIP), bombesin, neurotensin, and substance P (SP). See, generally, *Textbook of Clinical Chemistry*, N. W., Ed., W. B. Saunders Co., Philadelphia, Pa., pp. 1000–1003.

The antigenic regions of a variety of peptide hormones, which may be used to prepare antigenically active fragments, are disclosed, for example, in Lincoln et al., *Rec. Prog. Horm Res.* 36:1 (1980); Nakao, K., et al., *Biochim. Biophys. Res. Commun.*, 124:815 (1984); Dzau, V. J., et al., *Clin. Exp. Hypertens.*, A5(7&8):1207 (1983); and Tanaka, I., et al., *Biochim. Biophys. Res. Commun.*, 124:663 (1984).

In addition, the antigenic region of the hepatitis B surface antigen may be used to prepare a chimeric protein which can be used to detect antibodies to hepatitis. An antigenically active epitope of hepatitis surface protein is disclosed, for example, by Neurath, U.S. Pat. No. 4,591,552 (1986). Antibodies specific for HBsAg peptides are disclosed, for example, by Dreesman, G. R., et al., *Nature* 295:158–160 (1982).

In a further embodiment, the antigenic peptide comprises an epitope or antigenic determinant of a viral protein, e.g., the HIV diagnostic peptides p18, p24, gp41 and gp120. An antigenic peptide of gp41 is disclosed, for example, by Gnann, J. W., Jr., et al., *Science* 237:1346–1349 (1987).

Aequorin Photoprotein

Aequorin, a preferred photoprotein of the invention, is a photoprotein of about 21,000 daltons. It exists in two forms, the aequorin form which is capable of luminescence with bound luciferin, and apoaequorin, which is the photoprotein without bound luciferin. The addition of Ca$^{++}$ to aequorin triggers the emission of light at 470 nm. The emission of light is accompanied by the oxidation of the luciferin. Discharged aequorin may be regenerated by the addition of any of the chemically related luciferin compounds such as synthetic coelenterate luciferin, or coelenterazine, in the presence of dissolved oxygen, and 2-mercaptoethanol. The addition of calcium ions to the regenerated aequorin will again trigger the emission of light. Prasher et al, *Biochem. and Biophys. Res. Comm.* 126 3:1259–1268.

The luciferin compounds may be prepared according to the methods disclosed by Hori, K., et al., *Biochemistry* 14:2371–2376 (1975); Hori, K., et al., *Proc. Natl. Acad. Sci. (USA)* 74:4285–4287 (1977); and Inoue, S., et al., *Chem. Lett.* 141–144 (1975). Renilla luciferin may be isolated from *Renilla reniformis* by using the modified procedure of Hori et al., disclosed in Example 2 below.

Production of Chimeric Proteins

The DNA sequences of the aequorin and other luciferases employed for preparation of the chimeric proteins of the invention may be derived from a variety of sources. For example, mRNA may be isolated from the jellyfish *Aequorea victoria*, Faust, C. H., et al. *Biochem.* 18:1106–1119 (1979) and converted to copy DNA (cDNA) by known reverse transcriptase methods. Gubler et al., *Gene* 25: 263–269 (1983), Prasher, D., et al., *Biochem. Biophys. Res. Commun.* 126:1259–1268 (1985). Firefly luciferase cDNA may be prepared from RNA using the methods of De Wet, J. R., et al., *P.N.A.S. (USA)* 82:7870–7873 (1985).

The resulting cDNA may be packaged into a commercially available lambda phage. Huhynh, T. V., et al., *DNA Cloning—A Practical Approach* 1:49–78, Glover (Ed), IRL Press, Washington D.C. The particular phage containing mRNA encoding aequorin may be selected for by the use of synthetic DNA hybridization probes specific for a short sequence of the aequorin gene. Such selected cDNA may then be inserted into a commercially available plasmid, amplified, and then inserted into a second plasmid obtained from M. Neuberger. This pSV-V$_{NP}$ plasmid encodes for an immunoglobulin specific for the antigen 4-hydroxy-3-nitrophenyl (NP). The genetic sequence for aequorin may be inserted by known methods of genetic manipulation into the pSV-V$_{NP}$ plasmid in the proper location to create a continuous polypeptide immunoglobulin subchain with an aequorin sequence replacing the immunoglobulin F$_c$ region.

Other DNA sequences which encode other variable sequences may then be inserted using suitable ligases. Methods for preparation of recombinant monoclonal antibodies having specificity to an antigen of choice are disclosed, for example, by Oi and Morrison, *BioTechniques* 4:214–221 (1986). Examples of antibodies with various specificities which may be used in the practice of the invention are listed, for example, in Linscott's *Directory of Immunological and Biological Reagents*, 4th Ed., 1–23 (1986–1987).

The expression plasmid which codes for an immunoglobulin where the F$_c$ protein is substituted with a nuclease (pSV-V$_{NP}$ gamma SNase) was disclosed by Neuberger, M. S., et al., *Nature* 312:604–608 (1984); see also PCT Application WO 86/01533. The DNA restriction fragment containing the aequorin or luciferase gene may be inserted into the XhoI site located in the CH$_2$ exon of the mouse gamma 2b gene as described for construction of the plasmid pSV-V$_{NP}$ gamma SNase or plasmid pSV-V$_{NP}$ gamma Klenow (see PCT Application, Publication No. WO86/01533).

The resulting genetic constructs may be joined together to form a single DNA segment or may be maintained as separate segments, by themselves or in conjunction with vectors and become joined as one continuous polypeptide during transcription (DNA to RNA step).

An alternative method of obtaining aequorin DNA is to isolate genomic (chromosomal) DNA from species which produce photoproteins, fragment the DNA with one or more restriction endonucleases, and then clone and screen the resulting DNA fragments with a hybridization probe as described above.

Genetic Controls

In order for the host cell to successfully express the chimeric proteins, transcriptional and translational signals recognized by the host must be installed at the proper locations in the DNA of the vector. The vector ordinarily carries a bacterial replicon site, as well as specific genes which are capable of providing phenotypic selection in transformed cells. The expression of a chimeric molecule could also be placed under control of regulatory sequences recognized by *E. coli*, for example, the tryptophan promoter from the Trp E gene of *E. coli*, inducible by the addition of beta indole acrylic acid (a tryptophan analog). The expression of chimeric molecules in such a way would require a chimeric gene without intron sequences, unlike p205 GTi.

Other promoter/operator systems or portions thereof can be employed as well. For example, those of colicin E1, galactose, alkaline phosphatase, lactose, xylose, tax, and the like can be used.

In a mammalian host, additional elements will also be needed for optimal synthesis of mRNA transcribed from the inserted vector within the host. These elements may include splice signals, as well as transcription promoters, enhancers, and termination signals. The cDNA expression vectors incorporating such elements include those described by Okayama, H., *Mol. Cel. Biol.* 3:280 (1983), and others. Many of these elements are present in the vector described because the gene elements have been isolated from mammalian cells.

The transcriptional and translational signals may be derived from viral sources, such as retroviruses (RSV, MMTV and MoMLV), adenovirus, bovine papilloma virus, simian virus. Alternatively, promoters from mammalian expression products, such as actin, collagen, myosin, etc., may be employed. Transcriptional initiation signals may also be selected which allow for repression or activation, so that expression of the genes may be modulated by temperature or chemical signals.

For a mammalian host, several possible vector systems are available for expression. One class of vectors utilizes DNA elements which are derived from animal viruses such as bovine papilloma virus, polyoma virus, adenovirus, retroviruses (RSV, MMTV or MoMLV), or SV40 virus.

Host Cells

The preferred hosts for chimeric protein production are mammalian cells, grown in vitro in tissue culture or in vivo in animals. Mammalian cells provide post-translational modifications to immunoglobulin protein molecules including correct folding or glycosylation of the correct sites. Mammalian cells which may be useful as hosts include cells of fibroblast origin such as VERO or CHO-K1, or cells of lymphoid origin, such as the hybridoma SP2/O-AG14 or the myeloma P3x63Sgh, and their derivatives. Alternatively, nonmammalian cells may be employed, such as bacteria or fungi. Where the chimeric protein is not glycosylated, any host may be used to express the protein which is compatible with replicon and control sequences in the expression plasmid.

Where the host cells for immunoglobulin production are immortalized cells, primarily myeloma or lymphoma cells, such cells may be grown in an appropriate nutrient medium in culture flasks or injected into a syngeneic host, i.e., mouse or rat, or immunodeficient host or host site, e.g., nude mouse or hamster pouch. In particular, the cells may be introduced into the abdominal cavity of an animal to allow production of ascites fluid and harvesting of the chimeric antibody. Alternatively, the cells may be injected subcutaneously and the antibodies harvested from the blood of the host. The cells may be used in the same manner as the hybridoma cells. See Diamond et al., *N. Eng. J. Med.* 304:1344 (1981), and Kennett, McKearn and Bechtol (eds.), *Monoclonal Antibodies: Hybridomas—A New Dimension in Biologic Analysis,* Plenum, 1980.

Transfection

Once host cell type is selected and the vector or DNA sequence containing the constructs has been prepared for expression, the DNA constructs may be introduced to an appropriate host. Various techniques may be employed, such as protoplast fusion, calcium phosphate precipitation, electroporation or other conventional techniques. Recent techniques for the stable introduction of immunoglobulin genes into myeloma cells are discussed in Banerji, J., et al., *Cell* 33:729–740 (1983); and Potter, H., et al., *Proc. Nat'l Acad. Sci.* (USA) 81:7161–7165 (1984).

After the transfection, the cells are grown in media selective for the selection marker on the vector, in this case, *E. coli* gpt gene conferring resistance to mycophenolic acid in the presence of xanthine and hypoxanthine, and screened for appropriate activities. Expression of the gene(s) results in production of the chimeric protein.

The chimeric proteins of the invention may be isolated and purified in accordance with conventional conditions, such as extraction, precipitation, chromatography, affinity chromatography, electrophoresis, or the like.

Assays

The chimeric proteins of the invention may be used in any known assay where a labeled antibody, labeled antigen, or other specific binding protein system is conventionally used. Such assays include homogeneous assays, heterogeneous assays, sandwich assays, reverse assays, and competitive assays.

Broadly, the assays are based upon the formation of a complex between an antigenic substance or antibody being assayed and a labeled antibody or antigenic substance. The luminescent activity of the photoprotein portion of the chimeric protein of the invention, when complexed to the antigen or antibody being assayed and/or the photoprotein portion of the unbound chimeric protein, permits detection and/or quantitation of the amount of complex in the sample.

Broadly, the method for detection of an analyte of interest comprises the steps of contacting a chimeric protein as described above having binding specificity for an analyte of interest with a sample containing the analyte of interest and thereby forming a mixture containing chimeric protein-analyte of interest complex and unbound chimeric protein. The analyte of interest may be an antibody, an antigen, a hapten, an antigenic determinant, an epitope or some portion thereof. After the complex has been formed, the photoprotein portion of the complex and/or of the unbound chimeric protein is caused to luminesce and thereby indicate the presence of the analyte of interest. The luminescence can be detected and the information detected can be recorded or otherwise processed to determine the presence of and/or the amount of the analyte of interest. As will be understood by those skilled in the art, many variants of the assay methods may be performed without departing from the invention.

The photoprotein portion of unbound chimeric protein or chimeric protein bound to another binding substance is caused to luminesce in the presence of luciferin and calcium ion. The luciferin may be bound to the chimeric protein to form a chimeric protein-luciferin complex which complex is then used in the assay. Alternatively, luciferin may be added to a sample containing analyte of interest together with chimeric protein to form a chimeric protein-luciferin-analyte of interest complex, or, may be added to a sample after the chimeric protein has been introduced and after the chimeric protein-analyte of interest complex has been formed. In such latter case, from ten minutes to two hours may be required to form the chimeric protein-luciferin-analyte of interest complex. Luciferin is typically employed in concentrations of at least one mg/liter. An effective amount of calcium ion is then added to the mixture being assayed or to one or more components thereof to cause the photoprotein to luminesce. The calcium may be added in molar excess with respect to the luciferin, e.g., in concentrations of 15–20 mg/liter, in order to drive the luminescence reaction to completion.

The chimeric proteins of the invention may be used in a homogeneous assay to detect endogenous antibodies where the binding of the antibody to the antigenic peptide causes a change in the luminescent properties of the photoprotein. This change may be the result of a steric-induced conformational change of the photoprotein-luciferin complex.

The assay techniques are based upon the formation of a complex between the antigenic substance being assayed and an antibody or antibodies in which one or the other member of the complex may be detectably labeled. The luminescent activity of the photoprotein present as part of the antigen-antibody complex is a direct measure of the amount of the antigenic substance in a sample.

In a sandwich immunometric assay, a quantity of unlabeled antibody is bound to a solid support which is insoluble in the fluid being tested. This immobilized antibody, which is specific to the antigen of interest, is first contacted with the sample being tested so that a binary antigen-antibody complex is formed. After a suitable incubation period, the solid support is washed to remove unbound antigen, then contacted with a solution containing a known quantity of a labeled antibody which is specific to the antigen. After a second incubation period, the solid support is then washed a second time to remove the unreacted labeled antibody. This type of assay is frequently referred to as a two-site or sandwich assay, since the antigen has two antibodies bonded to its surface at different locations. For general sandwich immunoassay technique, see David et al., U.S. Pat. No. 4,376,110. In this invention, the chimeric protein comprising a photoprotein is substituted for the labeled antibody of the traditional immunoassay.

To eliminate at least one of the washing steps associated with this procedure, simultaneous and reverse assays may be used. A simultaneous assay involves a single incubation step as the antibody bound to the solid support and the labeled chimeric antibody are both added to the sample being tested at the same time. After incubation, the solid support is washed to remove unbound analyte and unbound labeled antibody, and the bound antibody-analyte-chimeric antibody "sandwich" is detected as with a conventional "forward" sandwich assay.

A reverse assay involves the stepwise addition of a solution of chimeric antibody to the fluid sample, incubation of that mixture, and addition of unlabeled antibody bound to a solid support. After a second incubation, the solid phase is washed in conventional fashion and the amount of labeled complex is detected by use of a luminometer. See U.S. Pat. No. 4,098,876 to Piasio et al.

In a competition immunoassay, an antigenic substance in a sample fluid being tested for its presence competes with a known quantity of chimeric labeled antigen for a limited quantity of antibody binding sites on a complementary binding material. The amount of labeled antigen bound to the complementary binding material is inversely proportional to the amount of antigen in the sample. A chimeric protein comprising a photoprotein and an antigenically active peptide or antigen may be used in place of the traditional labeled antigen.

In the competitive immunoassays using the chimeric proteins of the invention, a chimeric protein having an amino acid sequence which provides binding specificity for a complementary material and which is capable of competing with the analyte of interest for binding sites on the complementary material, is contacted with a sample of the substance containing the analyte of interest in the presence of the complementary material. The assay conditions are conducive to cause the chimeric protein and the analyte of interest to competitively bind to the complementary material. A mixture containing (i) analyte of interest-complementary material, (ii) chimeric protein-complementary material complex, and (iii) unbound chimeric protein is formed. The photoprotein in the chimeric protein-complementary material complex formed, or in unbound chimeric protein, can be caused to luminesce according to the methods described above and the luminescence can be detected to determine the presence of the analyte of interest by measurements relating to that luminescence.

The assay methods of the invention also include assays which rely primarily on the specific binding properties of avidin and streptavidin. Broadly, such methods may be used for the detection or quantitation of an analyte of interest and include the steps of contacting a chimeric protein as described above which contains avidin or streptavidin with a sample containing a biotin-labeled analyte of interest. A chimeric protein-biotin labeled analyte of interest complex is thereby formed and by causing the photoprotein portion of that complex and/or the photoprotein portion of unbound chimeric protein to luminesce, the presence of the analyte of interest can be detected.

Methods of the invention employing the specific binding affinities of avidin and streptavidin are particularly useful in methods for the detection or quantitation of a nucleic acid analyte of interest. In such method, the sample containing the nucleic acid analyte of interest is contacted with a biotinylated nucleic acid probe having specificity for the analyte of interest. The hybridized biotinylated probe formed thereby is contacted with a quantity of chimeric protein containing avidin or streptavidin thereby forming a mixture containing chimeric protein-biotin labeled hybridized probe complex and unbound chimeric protein. By causing the photoproteins of the complex and/or the unbound chimeric protein to luminesce, one can determine the presence and/or the quantity of the nucleic acid analyte of interest. Where the nucleic acid analyte of interest is bound to a solid phase, the solid phase is first washed to remove unhybridized biotinylated probe prior to contact with the chimeric protein. Where the nucleic acid analyte of interest is in solution, the hybridized and unhybridized probes are separated prior to contacting the former with the chimeric protein.

A sandwich assay can be advantageously conducted by contacting a sample containing analyte of interest with a solid phase complementary material having binding specificity for that analyte of interest and thereby forming a complementary material-analyte of interest complex; washing the solid phase to remove unbound components of the sample; contacting the solid phase with a quantity of a biotin-labeled antibody to the analyte of interest and thereby forming a sandwich; washing the sandwich to remove unbound biotin-labeled antibody; and thereafter contacting the sandwich with a chimeric antibody containing avidin or streptavidin, and thereby forming a mixture containing sandwich bound to chimeric protein and unbound chimeric protein. By pursuing the further steps of washing the sandwich to remove unbound chimeric antibody and thereafter causing the photoprotein portion of the sandwich and/or the photoprotein portion of unbound chimeric protein to luminesce, one can detect by that luminescence the presence and/or amount of the analyte of interest.

Competitive immunoassays employing chimeric photoproteins containing avidin or streptavidin are also advantageously conducted. In such immunoassays, a sample of the substance being analyzed and containing an unknown quantity of analyte of interest is contacted with a known quantity of biotin-labeled analyte of interest and a solid phase complementary material. The biotin-labeled analyte of interest and the analyte of interest compete for binding sites on the complementary material. After washing the solid phase to remove unbound components of the sample, the solid phase may be contacted with a quantity of chimeric protein of the invention containing avidin or streptavidin to form a biotin-labeled analyte of interest-chimeric protein complex. That complex can be detected by the several alternative procedures of the invention.

In still another competitive immunoassay employing chimeric photoproteins containing avidin or streptavidin, the assays are performed in the presence of a solid material. A liquid sample containing an unknown quantity of an analyte of interest and further containing a known quantity of complementary material comprising biotin-labeled antibody having specificity for the analyte of interest, is contacted with the solid material having bound thereto a known quantity of analyte of interest. The mixture is incubated under conditions which permit the competitive binding of biotin-labeled antibody to the free analyte of interest and to the bound analyte of interest, thereby forming a mixture containing solid phase analyte of interest-biotin-labeled antibody complex. Thereafter, the solid phase is washed to remove unbound components and then incubated with chimeric protein containing avidin or streptavidin. Such incubation forms a mixture containing solid biotin-labeled antibody-analyte of interest-chimeric protein complex, and unbound protein. The photoprotein portion of the complex and/or the photoprotein portion of unbound chimeric protein is then caused to luminesce and by detection of the luminescence and correlation of that luminesce with standards, the presence of the analyte of interest can be determined.

The assay methods of the invention also include assays which rely primarily on the specific binding properties of protein A. Broadly, such methods may be for the detection of quantitation of an antibody and comprise the steps of contacting a chimeric protein as taught above which contains protein A with a sample containing an antibody and forming thereby a mixture containing chimeric protein-antibody complex, and, unbound chimeric protein. By then causing the photoprotein portion of the complex and/or the photoprotein portion of unbound chimeric protein to luminesce, and correlating the luminescence with known standards, the presence of the antibody or quantity thereof may be determined.

A sandwich assay employing chimeric protein containing protein A may be advantageously carried out by contacting a sample with a solid phase complementary material having binding specificity for an analyte of interest and thereby forming a solid phase complementary material-analyte of interest complex; washing the solid phase to remove unbound components of the sample; contacting the solid phase with a quantity of antibody to the analyte of interest, and thereby forming a solid phase complimentary material-analyte of interest-antibody sandwich; washing the solid phase to remove unbound antibody; contacting the solid phase with a chimeric antibody containing protein A and thereby forming a mixture containing the sandwich bound to chimeric protein and unbound chimeric protein; washing the solid phase to remove unbound chimeric protein; causing the photoprotein portion of the sandwich and/or the photoprotein portion of unbound chimeric protein to luminesce; and by detection of the luminescence and correlation of same with standards, determining the amount of the analyte of interest.

A competitive immunoassay involving chimeric proteins containing protein A may be performed in the presence of a solid material for the detection or quantitation of an analyte in a substance. The competitive immunoassay includes the steps of contacting a liquid sample of the substance containing an unknown quantity of the analyte, and a known quantity of a complementary material having binding specificity for the analyte and having binding specificity for protein A, with a solid material having bound thereto a known quantity of the analyte. This system is permitted to incubate under conditions conducive to the competition binding of the complementary material to the free analyte and to the bound analyte such that a solid phase bound analyte-complementary material complex is formed. The solid phase is then washed to remove unbound components and then incubated with a quantity of chimeric protein containing protein A such that a solid phase bound analyte-complementary material chimeric protein complex is formed. By causing the photoprotein portion of that latter complex, and/or, the photoprotein portion of unbound chimeric protein to luminesce, one can detect or quantitate by suitable correlation the presence of the analyte of interest.

The chimeric antibody of the invention can also be used as a luminescent stain for tissue sections. For example, a chimeric antibody may be constructed which is specific for epitopes or antigenic determinants of cancer cells. The chimeric antibody may then be applied to a tissue section obtained from a biopsy to confirm the presence of the cancerous tissue using techniques known to the art for applying labeled antibody reagents to tissue or cells to be viewed microscopically. A chimeric antibody label for microscopic use does not have some of the disadvantages of the prior art labeled antibody reagents, such as unreliable localization, and steric interference by the label side chain with proper localization. They are also easier to prepare. The chimeric antibody may also be used as an imaging agent to localize tumors in vivo.

In a preferred embodiment, a chimeric protein comprising one or more epitopes or antigenic determinants of a viral protein, e.g., the HIV diagnostic peptides, may be used to detect antibodies which are associated with infection by HIV. Such an assay may comprise contacting a biological sample suspected of containing antibodies to HIV with the chimeric protein comprising one or more epitopes of the HIV diagnostic proteins, and detecting whether a complex has formed. The biological sample may comprise any body fluid which contains HIV antibodies. Such body fluids include, but are not limited to, blood, sera, cerebral-spinal fluid, sputum, urine, amniotic fluid, or other puncture fluids.

The antibody-antigen complex may be, for example, physically separated and the complex detected and quantified. The sample containing the HIV-antibody-fusion protein complex may be treated with an immobilized antibody which is specific for the endogenous HIV specific antibody, e.g., anti-IgM, anti-IgG, anti-IgE, anti-IgA, and anti-IgD antibodies and the like. Such anti-immunoglobulin antibodies may be monoclonal or polyclonal. The solid support may then be washed with suitable buffers to give the immobilized HIV-antibody chimeric protein complex. The photoprotein may be detected by adding coelenterazine and then calcium ion, and then detecting the emitted light and thereby the HIV-antibody.

The following examples are illustrative, but not limiting, of the method and composition of the present invention. Other suitable modifications and adaptations which are obvious to those skilled in the art are within the spirit and scope of this invention.

EXAMPLES

Materials

Restriction enzymes, reagents for generation of cDNA and all radioisotopes were purchased from Amersham (Arlington Heights, Ill.). The oligo (dT)-cellulose, some restriction enzymes, and oligo nucleotide linkers were purchased from Bethesda Research Laboratories (Gaithersburg, Md.) and Biolabs (Beverly, Mass.). The reagents for the lambda phage cloning were purchased from Stratagene (San Diego, Calif.).

Example 1

Cloning of Aequorin

A. Isolation of RNA

The jellyfish *Aequorea victoria* were collected at Friday Harbor laboratories, University of Washington. The outer margin of the umbrella of the jellyfish was excised with a cutting machine essentially as described by Johnson and Shimomura (Johnson, F. G., et al., *Methods in Enzymol.* 57:271–291 (1978)). Twenty outer margins were solubilized in 30 ml of 4 M guanidinium thiocyanate/50 mM Tris CL (pH 7.6) 10 mM EDTA/2% w/v sodium lauryl sarkosinate/1% v/v 2-mercaptoethanol and heated to 50–60° C. with shaking for 10 min. To this mixture 30 ml of phenol, preequilibrated with 0.1 M Tris Cl (pH 8.0)/0.2% 2-mercaptoethanol and heated to 50–60° C., was added and shaken for 5–10 min followed by the addition of 15 ml of 0.1 M $CH_3COONa$ (pH 5.2)/10 mM Tris Cl (pH 7.4)/1 mM EDTA. This mixture was extracted by addition of 30 ml of $CHCl_3$ with shaking for 10–15 min followed by centrifugation for 15 min at room temperature. The aqueous phase was recovered and reextracted with phenol/CHCl$_3$ as above. The aqueous phase was then added and the mixture stored at −70° C. and transported on dry ice. The RNA was recovered by centrifugation at 9,000×g in a Sorvall/HS4 rotor for 10 min at 4° C. This RNA was further purified by dissolving the pellet in 0.1 M Tris Cl (pH 7.4)/50 mM NaCl/10 mM EDTA/0.2% NaDodSO4/200 µg per ml proteinase K and incubated for 1–2 hours at 37° C. followed by extraction at 60° C. twice with an equal volume of phenol/CHCl$_3$ as above. The aqueous phase was then extracted twice with an equal volume of CHCl$_3$. The supernatant was then precipitated with ethanol. This RNA was then purified on oligo (dT) cellulose essentially as described by Faust, C. H., et al., *Biochemistry* 18:1106–1119 (1979), except that the buffer used for binding to the oligo (dT) cellulose was: 0.5 M KCl, 5 mM HEPES, pH 7.5; for washing; 0.1 M KCl, 5 mM HEPES, pH 7.5; for elution; 5 mM HEPES, pH 7.5. RNA was loaded at 5 mg/ml of oligo (dT) cellulose. The poly A+ RNA was precipitated with ethanol and stored at −70° C. Approximately 0.9 mg of RNA and 13 µg of poly (A) RNA per gram weight of outer margins was isolated. The results of this method for RNA isolation gave greater yields of RNA than previous methods, indicating the value of this method over those used previously, which yielded only 1.6 µg poly (A$^+$) RNA per gram of tissue (Prasher, D., et al., *Biochem. Biophys. Res. Commun.* 126:1259–1268 (1985)). This difference may reflect a better extraction methodology but could also be due to methods of tissue preparation and handling which are important factors in preparation of RNA.

B. cDNA Cloning

Double-stranded cDNA was prepared essentially as described by Gubler and Hoffmann (Gubler, U., et al., *Gene* 25:263–269 (1983)) using the reagents as provided by Amersham. Four µg of poly (A$^+$) RNA was converted to cDNA using avian myeloblastosis virus reverse transcriptase at 20 units/µg of RNA. This was followed directly by conversion to double-stranded cDNA using 4 units of *E. coli* ribonuclease H, and 115 units of *E. coli* DNA polymerase I. The double-stranded cDNA was rendered essentially blunt-ended by final treatment with 8 units of T4 DNA polymerase. The ligation of EcoRI linkers to double-stranded cDNA was done by previous methods (Kenten, J. H., et al., *P.N.A.S.* (*USA*) 79:6661–6665 (1982)). The Tinkered cDNA was size-fractionated on an agarose gel and cDNA of 400–2,000 base pairs isolated by electroelution onto NA45 paper (Schleicher and Schuell). The purified and Tinkered cDNA was then ligated to lambda-gt10 dephosphorylated arms (Stratagene) followed by in vitro packaging into lambda phage using Gigapack (Strategene) according to standard procedures (Huhynh, T. V., et al., *DNA Cloning—A Practical Approach* 1:49–78, Glover (ed.), IRL Press, Washington, D.C. (1985)).

C. Screening of the Phage cDNA Library and Vector Construction

The packaged phage were plated on C600Hfl-. The phage library was plated out and phage were replicated onto nitrocellulose filters for screening by hybridization using standard methods (Benton, W. D., et al., *Science* 196:180–182 (1977)). The probes were synthesized from synthetic oligo deoxynucleotides made on an Applied Biosystems machine to the aequorin gene sequence (Inouye, S., et al., *P.N.A.S.* (*USA*) 82:3154–3158 (1985)), to give:

5'ACAAGACAACATTTAGGATTTTGGTA-CACCATGGATCCTGCTTGCGAA AAGCTC-TACGGT and

5'GGTGTACCAAAATCCTAAATGTTGTCT-TGTCATCTCATCAACATCCGA GTTGTC-CACTTTC.

These oligodeoxynucleotides were labeled by nick translation with biotin 11-dUTP (Bethesda Research Laboratories) using standard methods (Maniatis, T., et al., *Molecular Cloning* (*A Laboratory Manual*), Cold Spring Harbor Laboratory (1982)). The unincorporated biotin was not removed from the reaction mix but was used directly on the prehybridized filters. After hybridization to the probe, the filters were developed using the avidin-alkaline phosphatase system (Bethesda Research Laboratories). The filters were incubated in 3% (w/v) bovine serum albumin (Fraction V), 0.1 M Tris-HCl (pH 7.5), 0.15 M NaCl at 65° C. for 1 hr followed by incubation with streptavidin-alkaline phosphatase conjugate at 1 µg/ml in 0.1 M Tris-HCl (pH 7.5), 0.15 M NaCl for 10 min at room temperature. The filters were then washed twice in 0.1 M Tris-HCl (pH 7.5), 0.15 M NaCl, washed in 0.1 M Tris-HCl (pH 9.5), 0.1 M NaCl, 50 mM MgCl$_2$, and then incubated with the substrates nitroblue tetrazolium (330 µg/ml) and 5-bromo-4-chloro-3-indolyphysphate (170 µg/ml) in the same buffer. The colonies showing the strongest signal were picked and subjected to two rounds of plaque purification and screening. The positive clones were cultured as plate lysates followed by phage purification using solid-phase anti-lambda-phage antibodies (LambdaSorb Promega Biotec, Madison, Wis.). The top agar from a 90 mm plate was removed and the phage eluted with 5 ml of phage buffer (Maniatis, supra) at room temperature for 30 min, followed by centrifugation to remove the debris. 50 µl of the solid phase was added to the supernatant followed by 30 min incubation on ice. The solid phase was then washed in phage buffer followed by specific elution of the phage with 0.5 ml of 10 mM Tris-HCl (pH 7.8), 10 mM EDTA and incubation at 70° C. for 5 min. After centrifugation, the supernatant was extracted with phenol/CHCl$_3$ using standard methods to obtain the DNA (Maniatis, supra). The phage DNA was then digested with EcoRI and inserts were subcloned into pUC18 (Norrander, J., et al., *Gene* 26:101–106 (1983)) at the EcoRI site. The methods used in the construction of the expression vectors were as previously described (Maniatis, supra).

Figure 1:
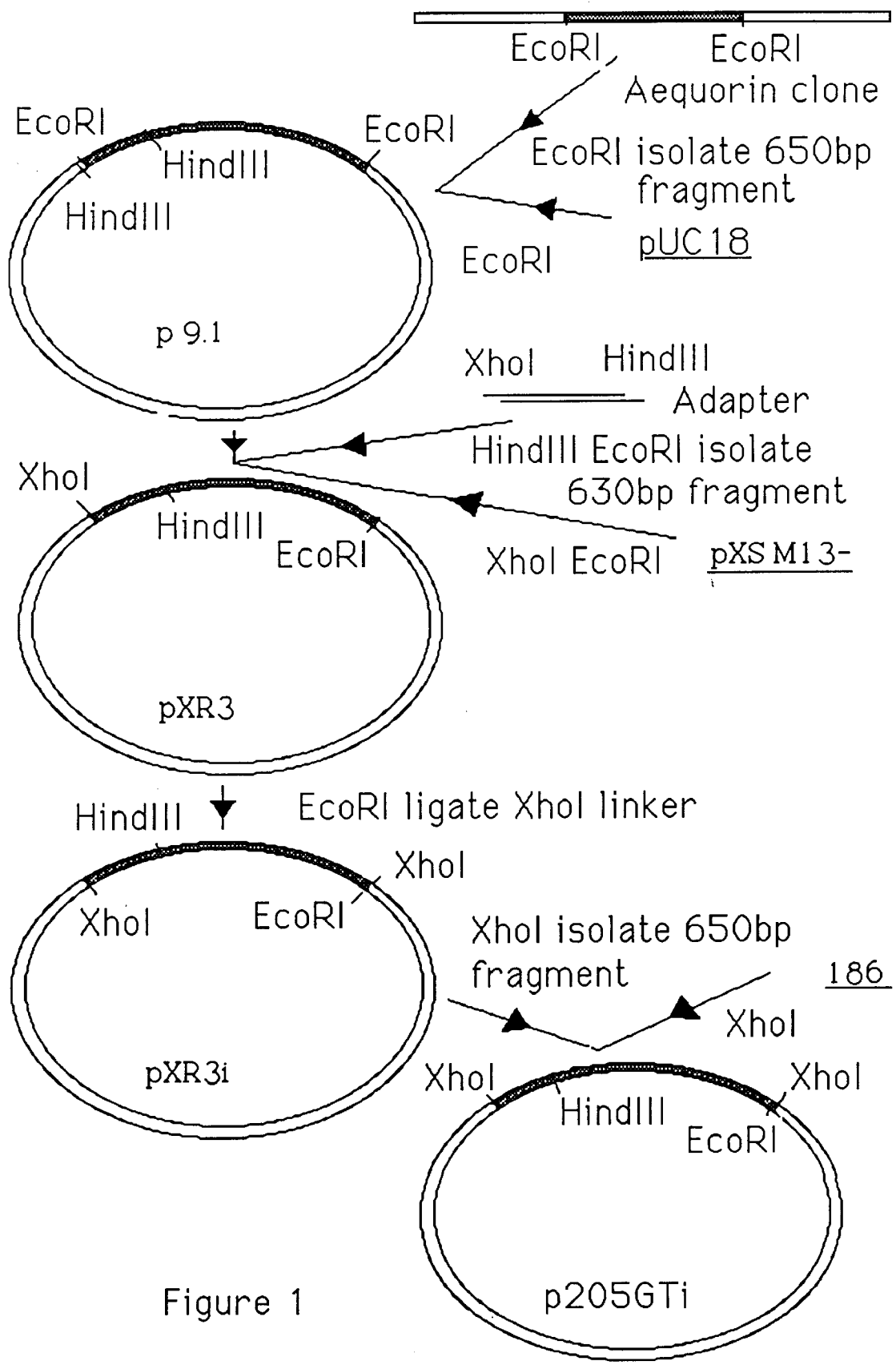
FIG. 1 depicts the scheme used to construct the plasmid p205GTi which contains the aequorin gene.

The yield of recombinant phage plated on C600Hfl-, which only allows growth of recombinant phage, showed a recovery of 5×10$^6$ clones per µg of poly (A)$^+$ RNA starting material. From the 8400 clones screened, 20 positive clones were identified using this method, indicating an abundance of 0.2% in the enriched gene library. From previous studies (Prasher, D., et al., *Biochem. Biophys. Res. Commun.* 126:1259–1268 (1983)), a level of 0.1% aequorin was found. This difference is most likely due to the size fractionation used in this study. We selected nine of the positive clones for further analysis by EcoRI digests. Three of these had inserts of the expected size (about 600 base pairs) and were subcloned into pUC18. The construction of the expression vectors is shown in FIG. 1 (see Example 4).

Example 2

Isolation of Renilla Luciferin

The coelenterate *Renilla reniformis* was collected at the Baruch Institute of Marine Biology, University of South Carolina, and transported back alive at room temperature, then frozen in liquid nitrogen and stored at −70° C. The luciferin was extracted using a modification of the method of Hori et al., *P.N.A.S.* (*USA*) 74:4285–4287. Frozen *Renilla reniformis* tissue was ground up with dry ice to give a fine powder, followed by the addition of 0.5 ml of 0.5 M EDTA and 1 ml of 1M HCl/gm of tissue and further grinding. The resultant powder was allowed to warm up and 10 ml of water/gm of tissue was added and the mixture transferred to a centrifuge tube for extraction with $CHCl_3$ (10 mL/mg of tissue), followed by pH adjustment to pH 5.5 using pyridine. The resultant extract was shaken for 10–15 min followed by centrifugation at 9000 g in a Sorvall/HS4 rotor and the $CHCl_3$ phase removed. The $CHCl_3$ extraction was repeated, and the $CHCl_3$ pooled. The $CHCl_3$ extracts were concentrated under reduced pressure (rotovap, Buchi) and the residue extracted with 1 M HCl/methanol (1 ml/4 gm of tissue) followed by lyophilization and storage under argon. This crude luciferin preparation was dissolved in 1 M HCl/methanol (1 ml/4 gm of tissue) for use in the aequorin photoprotein assay.

Example 3

Photoprotein Assay

The assay of bacterial extracts was performed essentially as described in Inouye et al. (*Biochemistry* 25:8425–8429 (1986)), but with the addition of 4 μl of luciferin extract per ml of extract. The culture supernatants from the transfected myeloma cell lines were diluted with assay buffer (30 mM Tris-HCl pH 7.6, 10 mM EDTA, 1% v/v 2-mercaptoethanol, 4 μl of luciferin extract per ml) and kept on ice for 2 hrs. The regenerated photoproteins from bacteria or myelomas were assayed in a Berthold luminometer, Biolumat LB 9500C (Berthold Instruments, Pa.) using 100 μl sample volumes and injection of 100 μl of 30 mM $CaCl_2$, 30 mM Tris-HCl (pH 7.6). The peak intensity was recorded, using the Berthold in its peak/autoinjection mode. Photoprotein samples were also assayed using the above-described methods and synthetic coelenterazine (London Diagnostics, Minneapolis, Minn.).

Example 4

A. Construction of the Antibody-Aequorin Fusion

The aequorin gene was isolated from the plasmid pXR3 as a XhoI fragment and ligated into the 186 vector to generate the plasmid p205GTi for expression of the antibody-aequorin chimeric on transfection of the J558L cell line. The 186 vector is the same as pSV-$V_{NP}$ gamma (CH2, CH3) disclosed by Neuberger in PCT Application, Publication No. WO86/01533, p. 25 (see Example 4—Fab-gamma-Klenow Chimeric Antibody). Vector 186 was also used in the construction of pSV-$V_{NP}$ SNase. The plasmid pSV-$V_{NP}$ gamma (CH2, CH3) was prepared by Neuberger from plasmid pSV2gpt which is deposited at the American Type Culture Collection, Rockville, Md., under accession number 37145.

Figure 2:
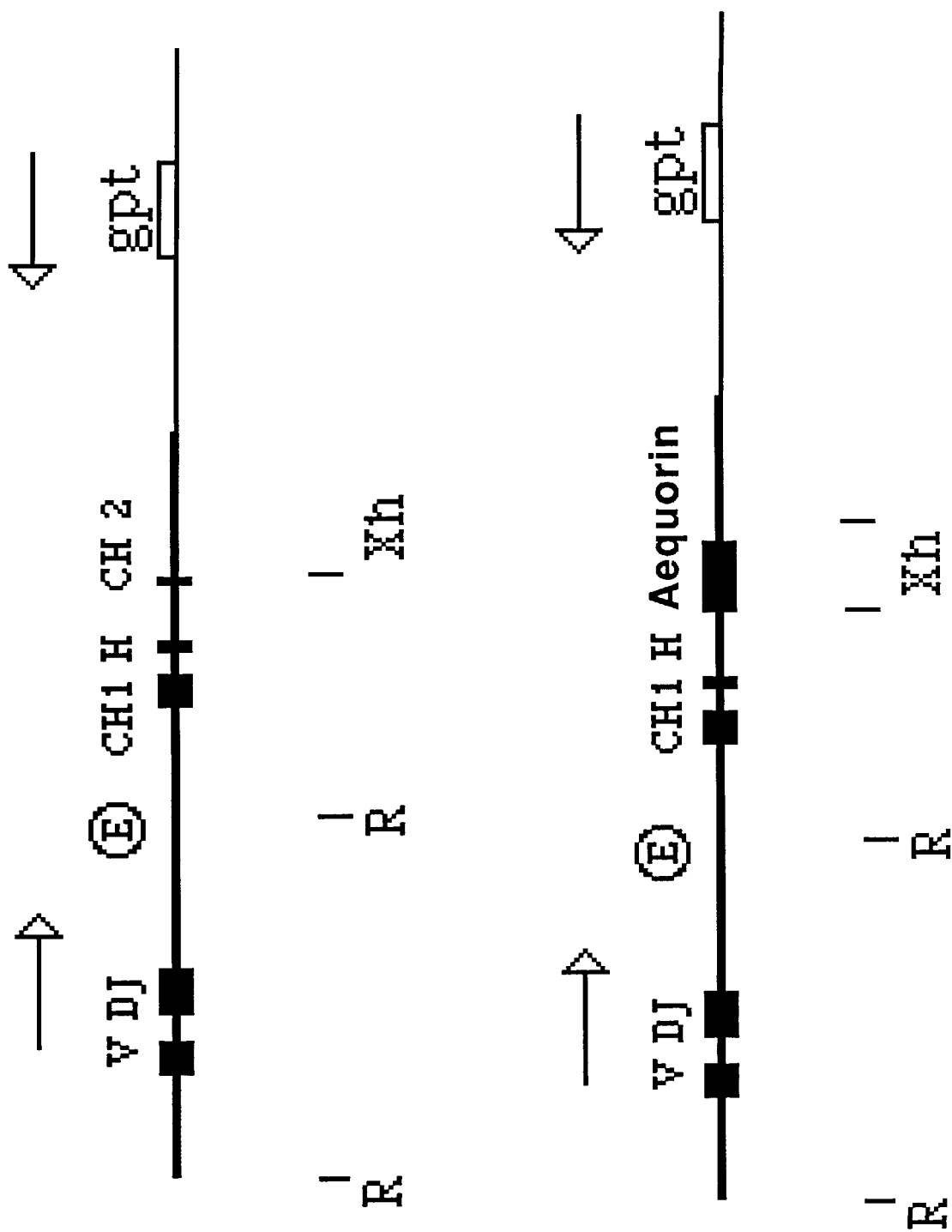
FIG. 2 depicts the structure of the plasmid 186 (pSV-$V_{NP}$) disclosed by Neuberger in comparison to plasmid p205GTi, which contains the aequorin gene.
Figure 3:
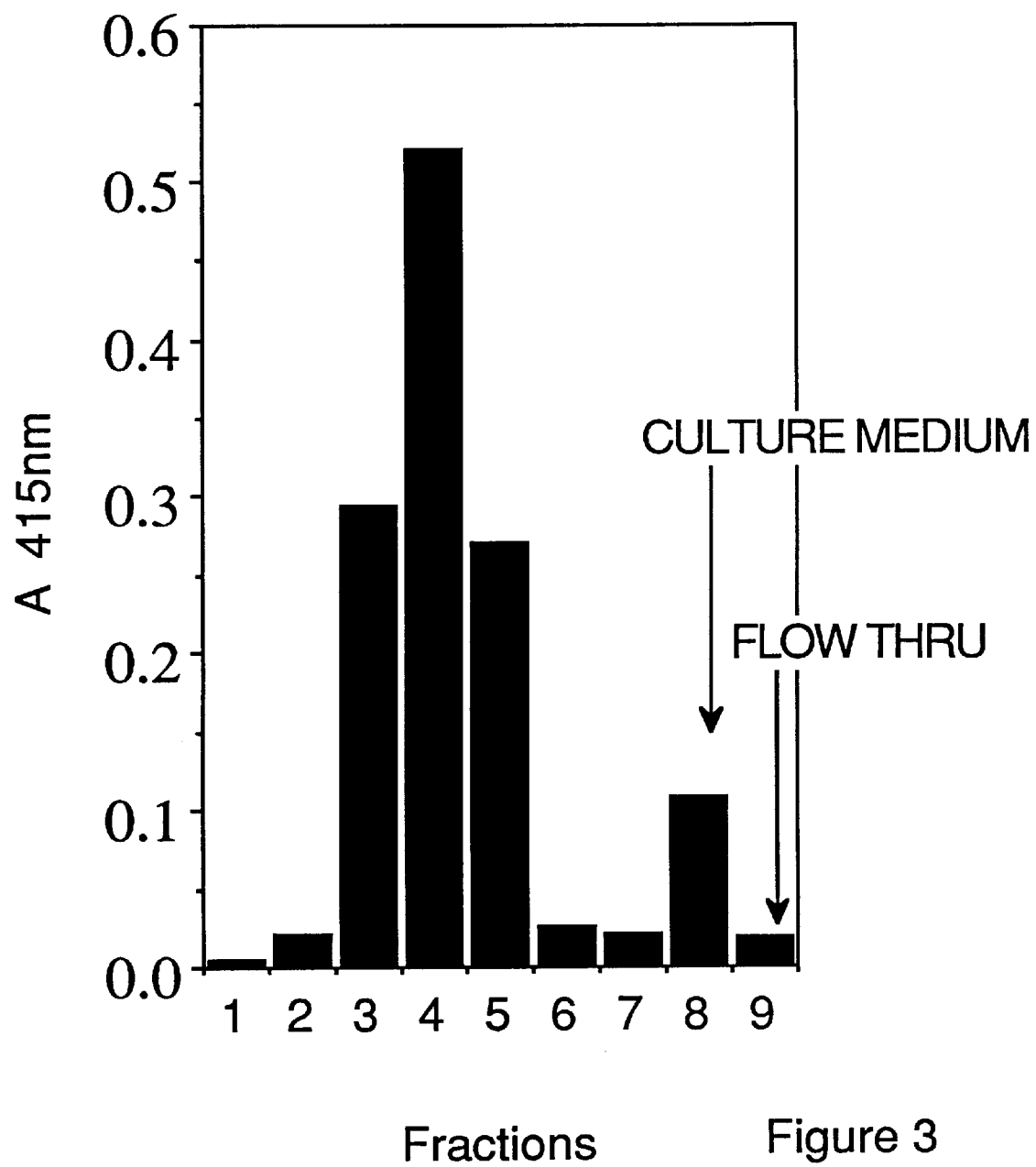
FIG. 3 depicts the enzyme linked immunoassay of chimeric aequorin-immunoglobulin fractions obtained by immunoaffinity chromatography.
Figure 4:
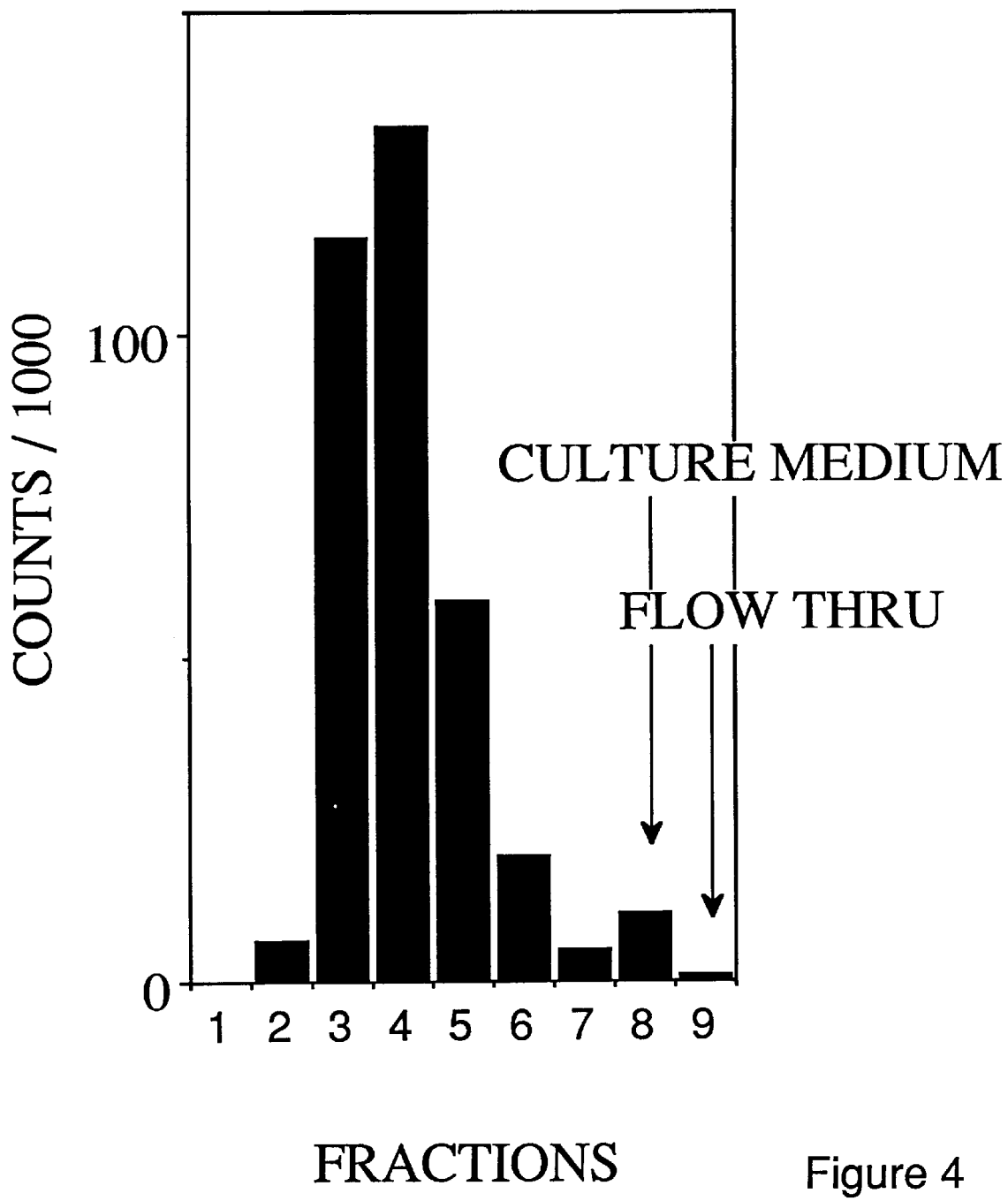
FIG. 4 depicts the light activity of fractions eluted from an NIP-immunoaffinity column.
Figure 5:
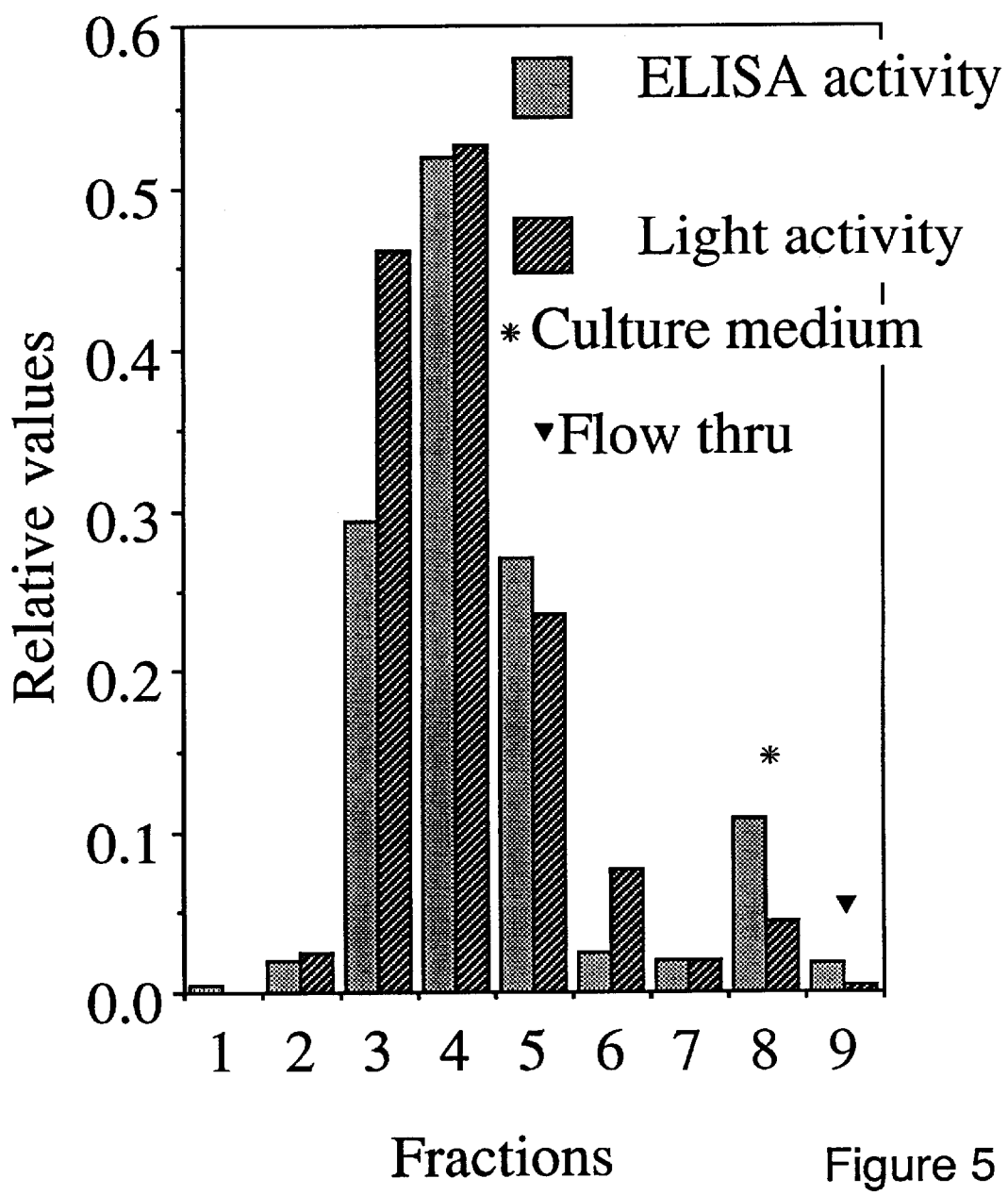
FIG. 5 depicts a comparison of the light activity against the ELISA activity of fractions eluted from an NIP-immunoaffinity column.
Figure 6:
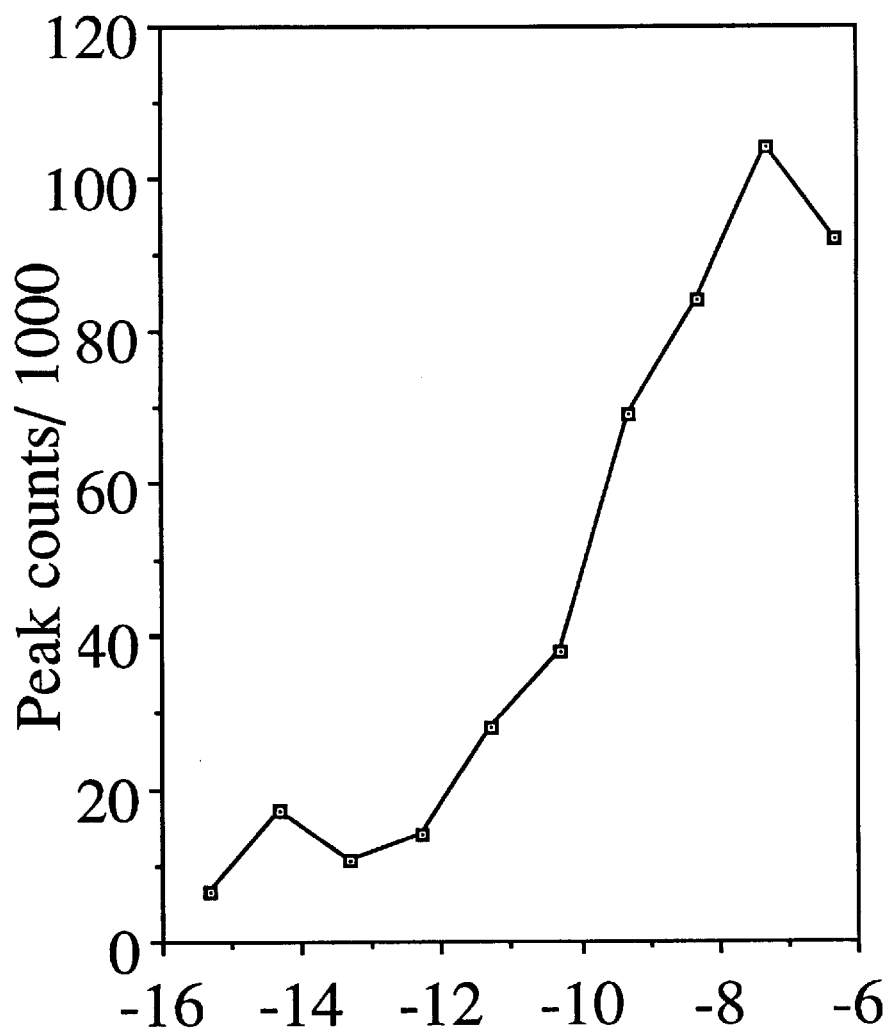
FIG. 6 depicts a graph of the amount of light activity against the log of the NIP concentration for the titration of immobilized NIP-BSA with aequorin-immunoglobulin chimeric protein.

The construction of the chimeric required modification of the EcoRI aequorin gene fragment in order to clone the gene into the XhoI site of the M. Neuberger vector 186 (FIG. 2). The overall scheme is depicted in FIG. 1. Initially, the aequorin gene was isolated as a HindIII 630 base pair fragment, removing the 5' end of the gene. This fragment was then ligated to an adapter sequence derived from the two oligos:

TCGAGACAAGCAAACAATACTCAGTCA and
CTGTTCGTTTGTTATGAGTCAGTTCGA.

Ligation of this adapter sequence tailors the aequorin gene as a XhoI-EcoRI fragment.

The aequorin gene, ligated to this adapter sequence, was then ligated into the vector pXS M13-, which was cut with XhoI and EcoRI, to give the vector pXR3. The vector pXS M13- was derived from pBS M13- (Stratagene, San Diego, Calif.) by introduction of a XhoI site in the M13 polylinker, by ligation in of an XhoI linker at the HincII site.

The plasmid pXR3 was then modified by the conversion of the EcoRI at the 3' end of the aequorin gene into the XhoI site, and by the ligation in of an XhoI linker to generate the plasmid pXR3i.

FIG. 2 shows a diagram of the basic structure of the parent plasmid 186 from M. Neuberger, and the derivative plasmid containing the aequorin gene, p205GTi. The arrows indicate the direction of transcription for the promoters driving expression of the gpt and antibody-aequorin genes. The elements of the immunoglobulin coding region are indicated by V, DJ, CH1, H and CH2. The enhancer element is indicated by the E.

The restriction sites are indicated by "R" for the EcoRI sites flanking the VH region and Xh for the XhoI sites.

B. Transfection of DNA into J558L Myeloma Cells

The plasmid p205GTi was then introduced into J558L myeloma cells, a mouse plasmacytoma expressing lambda-1 but not producing a heavy chain. See Oi et al., *Proc. Natl. Acad. Sci.* (*USA*) 80:825–829 (1983). The cell line J558L may be obtained from J558 (ATCC TIB6) by the methods disclosed by Coffino, P., et al., *P.N.A.S.* (*USA*) 68:219–223 (1971).

Cells at a density of approximately $10^6$/ml of growth medium (5% fetal calf serum in Iscove's modified Dulbecco's medium for hybridomas with penicillin and streptomycin added) were pelleted and washed with ice-cold phosphate buffered saline without $MgCl_2$ or $CaCl_2$ (PBS). After being repelleted, cells were suspended at a density of $10^7$/ml of PBS. The plasmid p205GTi, linearized by PvuI digestion, was added to the cell suspension at 10 μg/ml. 0.8 ml of this mixture was added to an electroporation cuvette and kept on ice for 10 min. The cells were then subjected to a high voltage pulse of 2.0 kV/cm at 25 μFD (t=0.7 ms) (Biorad, Gene Pulser) and immediately placed on ice for 10 min. Cells were then diluted with growth medium and cultured in 96-well microtitre plates. After incubation at 37° C., 5% $CO_2$ for 48 hrs, cells were selected by adding an equivalent volume of growth medium containing 200 μg/ml xanthine, 5 μg/ml mycophenolic acid, and 15 μg/ml hypoxanthine. ELISA assays were performed to screen for antibody production to the NIP haptin using NIP-BSH. Positive clones were then tested for the photoprotein activity as described. The clones positive for both activities were further analyzed with respect to the protein product and combined activities. Protein gel electrophoresis was conducted as described (Laemmli, U. K., *Nature* (*London*) 227:680–685 (1970). Approximately 100 anti-NP immunoglobulin positive clones/μg of plasmid DNA were obtained, with 1 cell in $10^4$ cells transfected to give a total of approximately 1000 clones. Four of the culture supernatants from the positive clones were found to have similar levels of activity (a range of twofold).

The DNA sequence of the gene construct, which allows expression of the variable NP sequence and aqueorin, appears in Table 1. See Neuberger, M. S., *EMBO J* 2:1373–1378 (1983); Bothwell, A. L. M., et al., *Cell* 24:625–637 (1981); Newell, N., et al., *Science* 209:1128–1132 (1980); Sakano, H., et al., *Nature* 286:676–683 (1980); Early, P., et al., *Cell* 19:981–992 (1980); Kim, S., et al., *Cell* 27:573–581 (1981); Gough, N. M., et al., *P.N.A.S.* (*USA*) 78:509–513 (1981); Gillies, S. D., et al., *Cell* 33:717–728 (1983); Banerji, J., et al., *Cell* 33:729–740 (1983); Gilliam, A. C., et al., *P.N.A.S.* (*USA*) 81:4164–4168 (1984); Takahashi, N., et al., *Gene* 11:117–127 (1980); Sakano, H., et al., *Nature* 286:676–683 (1980); Yamawaki-Kataoka, Y., et al., *Nature* 283:786–789 (1980); Tucker, P. N., et. al., *Science* 206:1303–1306 (1979); Ollo, R., et al., *Nature* 296:761–763 (1982); Tucker, P. S., et al., *Science* 206:1299–1303 (1979); Kataoka, T., et al., *P.N.A.S.* (*USA*) 76:4240–4244 (1979); and Zakut, R., et al., *Nucl. Acid. Res.* 8:453–466 (1980).

TABLE 1

SEQUENCE OF THE GENE CONSTRUCT TO ALLOW EXPRESSION OF THE VARIABLE NP SEQUENCE FUSED TO THE AEQUORIN GENE ON TRANSFECTION IN TO THE CELL LINE J558L OR OTHER CELL LINE EXPRESSING THE LAMBDA 1 LIGHT CHAIN

5'TRANSCRIPTIONAL CONTROL ELEMENT

AACTGTGTTACAGTGGGGCCACTGTCTCAGGATGCAAATCTTTTTAGTGCACAGGCT

CTAATGTTACCATCTATAGCCTCAACACAAAGTTGAGGGATGAGGTATGAGGTATG

AGGATGAATTTCCACAGAGAAGATTAGGACTGGGGCTTCAGAATCCTGATTCcTGAC

CCAGGTGTCCCTTCTTCTCCAGcAGGAGTAGGTGTTCATCTAATATGTATCCTGCTC

ATGAATATGCAAATCCTCTGAATCTACATGGTAAATATAGGTTTGTCTATACC

ACAAACAGAAAAACATGAGATCACAGTTCTCTCTACAGTTACTGAGCACACAGGAC

CTCACC

START OF CODING REGION
ATG

GGATGGAGCTGTATCATCCTCTTCTTGGTAGCAACAGCTACAGGTAAGGGGCTCACA

GTAGCAGGCTTGAGGTCTGGACATATATATGGGTGACAATGACATCCACTTTGCCTT

TCTCTCCACAGGTGTCCACTCCCAGGTCCAACTG

GENOMIC TO CDNA JUNCTION (V47 TO VB1-8)

cagcagcctggggctgagcttgtgaagcctggggcttcagtgaagctgtcctgcaaggcttctggctac accttcaccagctactggatgcactgggtgaagcagaggcctggacgaggccttgagtggattggaagg attgatcctaatagtggtggtactaagtacaatgagaagttcaagagcaaggccacactgactgtagac aaaccctccagcacagcctacatgcagctcagcagcctgacatctgaggactctgcggtctattattgt gcaagatacgattactacggtagtagctactttgactactggggccaaggcaccactctcacagtctcc tcaG

NP CDNA TO GENOMIC JUNCTION (JH2 CVNI)

gtgagtccttaaaacctctctcttctattcagcttagatagattttactgcatttgttgggggggaaatgt gtgtatctgaatttcaggtcatgaaggactagggacaccttgggagtcagaaagggtcattgggagccc tggctgatgcagacagacatcctcagctcccagacttcatggccagagatttatagggatcctggccag cattgccgctaggtccctctcttctatgctttctttgtccctcactggcctccatctgagataatcctgga gccctagccaaggatcatttattgtcaggggtctaatcattgttgtcacaatgtgcctggtttgcttactg gggccaagggactctggtcactgtctctgcaggtgagtcctaacttctcccattctaaatgcatgttggg gggattctgagccttcaggaccaagattctctgcaaacgggaatcaagattcaaccccttttgtcccaaa gttgagacatgggtctgggtcagggactctctgcctgctggtctgtggtgacattagaactgaagtatga tgaaggatctgccagaactgaagcttgaagtctgaggcagaatcttgtccagggtctatcggactct tgtgagaattaggggctgacagttgatggtgacaatttcagggtcagtgactgtcaggtttctctgaggt gaggctggaatataggtcaccttgaagactaaagaggggtccaggggcttttctgcacaggcagggaac agaatgtggaacaatgacttgaatggttgattcttgtgtgacaccaagaattggcataatgtctgagttg cccaagggtgatcttagctagactctggggtttttgtcgggtacagaggaaaaacccactattgtgatta ctatgctatggactactggggtcaaggaacctcagtcaccgtctcctcaggtaagaatggcctctccag gtctttatttttaacctttgttatggagttttctgagcattgcagactaatcttggatatttgccctgagg gagccggctgagagaagttgggaaataaatctgtctagggatctcagagcctttaggacagattatctc cacatctttgaaaaactaagaatctgtgtgatggtgttggtggagtccctggatgatgggatagggactt

TABLE 1-continued

SEQUENCE OF THE GENE CONSTRUCT TO ALLOW EXPRESSION OF THE VARIABLE NP SEQUENCE FUSED TO THE AEQUORIN GENE ON TRANSFECTION IN TO THE CELL LINE J558L OR OTHER CELL LINE EXPRESSING THE LAMBDA 1 LIGHT CHAIN tggaggctcatttgagggagatgctaaaacaatcctatggctggagggatagttggggctgtagttggag attttcagtttttagaatgaagtattagctgcaatacttcaaggaccacctctgtgacaaccattttatac agtatccaggcatagggacaaaaagtggagtggggcactttctttagatttgtgaggaatgttccacact agattgtttaaaacttcatttgttggaaggagctgtcttagtgattgagtcaagggagaaaggcatctag cctcggtctcaaaagggtagttgctgtctagagaggtctggtggagcctgcaaaagtccagctttcaaa ggaacacagaagtatgtgtatggaatattagaagatgttgcttttactcttaagttggttcctaggaaaa atagttaaatactgtgactttaaaatgtgagagggttttcaagtactcatttttttaaatgtccaaaattt ttgtcaatcaatttgaggtcttgtttgtgtagaactgacattacttaaagtttaaccgaggaatgggagtg aggctctctcataccctattcagaactgacttttaacaataataaattaagtttaaaatatttttaaatga attgagcaatgttgagttgagtcaagatggccgatcagaaccggaacacctgcagcagctggcaggaag caggtcatgtggcaaggctatttggggaagggaaaataaaaccactaggtaaacttgtagctgtggtttg aagaagtggttttgaaacactctgtccagccccaccaaaccgaaagtccaggctgagcaaaacaccac ctgggtaatttgcatttctaaaataagttgaggattcagccgaaactggagaggtcctcttttaacttatt gagttcaaccttttaattttagcttgagtagttctagtttccccaaacttaagtttatcgacttctaaaat gtatttagaagaattcaggcagaagaatagcttggctgcagagagtcctgggggccaggagagttgtcc gattgagcaggaacataggcaggaaaaggccctggcactgacattctcaagcaagccgtataagttaaa gttctagtgtcagaggcccaagctcggatcc

CH1 gccaaaacaacacccccatcagtctatccactggcccctgggtgtggagatacaactggttcctccgtg actctgggatgcctggtcaagggctacttccctgagtcagtgactgtgacttggaactctggatccctgt ccagcagtgtgcacaccttcccagctctcctgcagtctggactctacactatgagcagctcagtgactg tcccctccagcacttggccaagtcagaccgtcacctgcagcgttgctcacccagccagcagcaccacg gtggacaaaaaactt

INTRON ggtgagaggacattcaggggaggagggattcaccagagttgaggcaaaggtattagcctatctaaacca gccaggctgggatccatcaccaaggaggtgaccttagcccagggaagagggagatactgtctctgcctc cctcctgggaacatctagctatgaccacctacactcaaggacatgttcctctgggataggtgtgcttgtc atttccaggatcatcctggaactaagcccataccaggacaaactttcctctctctggtttggtgcttctc tccttcaaaaaccagtaacatccagccttctctctgca

HINGE gagcccagcgggcccatttcaacaatcaacccctgtcctccatgcaaggagtgtcacaaatgccca

INTRON ggtaagtcactaccagagctccactcccaggagaatggtaagtgctgtaaaaatccctgtaatgg aggataagccatgtacaaatccatttccatctctcctcatca

CH2 gctcctaacctc

TABLE 1-continued

SEQUENCE OF THE GENE CONSTRUCT TO ALLOW EXPRESSION OF THE
VARIABLE NP SEQUENCE FUSED TO THE AEQUORIN GENE ON TRANSFECTION IN
TO THE CELL LINE J558L OR OTHER CELL LINE EXPRESSING THE LAMBDA 1
LIGHT CHAIN

AEQUORIN

GAGACAAGCAAACAATACTCAGTCAAGCTTACATCAGACTTCGACAACCCAAGATG

GATTGGACGACACAAGCATATGTTCAATTTCCTTGATGTCAACCACAATGGAAAAA

TCTCTCTTGACGAGATGGTCTACAAGGCATCTGATATTGTCATCAATAACCTTGGAG

CAACACCTGAGCAAGCCAAACGACACAAAGATGCTGTAGAAGCCTTCTTCGGAGGA

GCTGGAATGAAATATGGTGTGGAAACTGATTGGCCTGCATATATTGAAGGAT

GGAAAAAATTGGCTACTGATGAGTTGGAGAAATACGCCAAAAATGAACCAACGCTC

ATCCGTATATGGGGCGATGCTTTGTTTGATATCGTTGACAAAGATCAAAATGGAGCT

ATTACACTGGATGAATGGAAAGCATACACCAAAGCTGCTGGTATCCAATCATCAGA

AGATTGCGAGGAAACATTCAGAGTGTGCGATATTGATGAAAGTGGACAACTCGATG

TTGATGAGATGACAAGACAACATTTAGGATTTTGGTACACCATGGATCCTGCTTGCG

AAAAGCTCTACGGTGGAGCTGTCCCCTAAGAAGCTCTACGGTGGTGATGCACCCTAG

GAAAGATGATG

Example 5

Construction and Expression of the HIV 1 Peptide-Aequorin Fusions

A. The HIV peptide gene sequences were incorporated into the NH terminus of the aequorin gene using the pXR3 vector cut at the HindIII and XhoI sites to allow the introduction of the synthetic oligonucleotides encoding for the HIV 1 peptide sequence derived from gp41. See Gnann, J. W., Jr., et al., *Science* 237:1346–1349 (1987). The first construct was generated using the two oligos:
AGCTTGACAGAGTACTGTTTAGAAGTG-CAGATCAGTTTACCAGAGCAACCCCAGAT ACCCAGCTGCTGGTC and ACCCAGCTGCTG-GTC and

TCGAGACCAGCAGCTGGGTATCTGGGGT-TGCTCTGGTAAACTGATCTGCACTTCTA AACAGTACTCTGTCA which allows the positioning of the HIV 1 peptide at the NH terminal residue after filling in the XhoI site. Expression is directed from the beta galactosidase promoter as in pBS M13-(Stratagene, San Diego, Calif.). The sequence of the construct pAA1 from the start codon for translation (in the pBS M13-vector), to the end of the aequorin gene is as shown below in Table 2.

TABLE 2

HIV-AEQUORIN 1

ATGACCATGATTACGCCAAGCTCGGAATTAACCCTCACTAAAGGGAACAAAAGCTT
-------- AIDS PEPTIDE -----------
Asp Gln Gln Leu Gly Ile Trp Gly Cys
GCATGAATGCAGGTAACTCGATCGA,GAC,CAG,CAG,CTG,GGT,ATC,TGG,GGT,TGC,
--------------------
Ser Gly Lys Leu Ile Cys
TCT,GGT,AAA,CTG,ATC,TGC,

ACTTCCTAAACAGTACTCTGTCAAGCTTACATCAGACTTCGACAACCCAAGATGGA

TTGGACGACACAAGCATATGTTCAATTTCCTTGATGTCAACCACAATGGAAAAATC

TCTCTTGACGAGATGGTCTACAAGGCATCTGATATTGTCATCAATAACCTTGGAGCA

ACACCTGAGCAAGCCAAACGACACAAAGATGCTGTAGAAGCCTTCTTCGGAGGAGC

TGGAATGAAATATGGTGTGGAAACTGATTGGCCTGCATATATTGAAGGATGGAAAA

AATTGGCTACTGATGAGTTGGAGAAATACGCCAAAAATGAACCAACGCTCATCCGT

ATATGGGGCGATGCTTTGTTTGATATCGTTGACAAAGATCAAAATGGAGCTATTAC

TABLE 2-continued

```
ACTGGATGAATGGAAAGCATACACCAAAGCTGCTGGTATCCAATCATCAGAAGATT

GCGAGGAAACATTCAGAGTGTGCGATATTGATGAAAGTGGACAACTCGATGTTGAT

GAGATGACAAGACAACATTTAGGATTTTGGTACACCATGGATCCTGCTTGCGAAAA

GCTCTACGGTGGAGCTGTCCCCTAAGAAGCTCTACGGTGGTGATGCACCCTAGGAAA

GATGATG
```

*E. coli* HB101 transformed with this plasmid was cultured in the presence of 20 mM isopropyl-D-thiogalactopyranoside (IPTG) for 4 hours at 37° C., harvested and stored at −70° C.

The pelleted bacteria were lysed with 40 μl of 9M urea and diluted to 1 ml with 30 mM Tris-HCl, 10 mM EDTA, 1% 2-mercaptoethanol; centrifuged for 5 min at 10,000 g and the supernatant stored at −70° C.

To assay for aequorin activity, 100 μl of the *E. coli* extract was activated with 6 ng of coelenterazine (London Diagnostics, Minneapolis, Minn.) for 2 hours at 0° C. These samples were then assayed in a Berthold luminometer (Biolumat luminescence analyzer LB 9500, Pittsburgh, Pa.) by injection of 100 μl of 30 mM Tris-HCL, pH 7.6, 30 mM CaCl$_2$ and measuring the peak intensity.

| Peak Counts From the Berthold | |
|---|---|
| control HB101 | 10 |
| clone 8 | 107,000 |
| clone 11 | 124,000 |
| clone 10 | 83,000 |
| clone 12 | 248 |

Clone 12 represents the gene before the polymerase filling to bring it into the correct reading frame. This is an indication of the level of misreading in the expression of a gene inserted in to a transcription unit. These results demonstrate the expression of the modified aequorin gene and recovery of its photoprotein activity.

B. A second construct was generated essentially as described above, but without filling in the XhoI site and not removing a number of the amino acids at the NH$_2$ terminus of the aequorin gene. The oligos used for this were:

TCGAGGACCAGCAGCTGGG-
TATCTGGGGTTGCTCTGGTAAACT-
GATCTGCGTCA and
AGCTTGACGCAGATCAGTTTACCAGAG-
CAACCCCAGATACCCAGCTGCTGGTCC.

The sequence of the second construct appears below (Table 3).

TABLE 3

HIV-AEQUORIN 1

ATGACCATGATTACGCCAAGCTCGGAATTAACCCTCACTAAAGGGAACAAAAGCTT
------------ AIDS PEPTIDE --------
Asp Gln Gln Leu Gly Ile Trp Gly Cys
GCATGAATGCAGGTAACTCGAT,  GAC,CAG,CAG,CTG,GGT,ATC,TGG,GGT,TGC,
--------------------
Ser Gly Lys Leu Ile Cys
TCT GGT AAA CTG ATC TGC

GTCAAGCTTACATCAGACTTCGACAACCCAAGATGGATTGGACGACACAAGCATAT

GTTCAATTTCCTTGATGTCAACCACAATGGAAAAATCTCTCTTGACGAGATGGTCT

ACAAGGCATCTGATATTGTCATCAATAACCTTGGAGCAACACCTGAGCAAGCCAAA

CGACACAAAGATGCTGTAGAAGCCTTCTTCGGAGGAGCTGGAATGAAATATGGTGT

GGAAACTGATTGGCCTGCATATATTGAAGGATGGAAAAAATTGGCTACTGATGAGT

TGGAGAAATACGCCAAAAATGAACCAACGCTCATCCGTATATGGGGCGATGCTTTG

TTTGATATCGTTGACAAAGATCAAAATGGAGCTATTACACTGGATGAATGGAAAGC

ATACACCAAAGCTGCTGGTATCCAATCATCAGAAGATTGCGAGGAAACATTCAGAG

TGTGCGATATTGATGAAAGTGGACAACTCGATGTTGATGAGATGACAAGACAACAT

TTAGGATTTTGGTACACCATGGATCCTGCTTGCGAAAAGCTCTACGGTGGAGCTGTC

CCCTAAGAAGCTCTACGGTGGTGATGCACCCTAGGAAAGATGATG

Example 6

Demonstration of the Combined Activities of the Aequorin-Antibody Fusion Protein A. Assay for NIP binding activity Microtitre plates were coated with 50 μl of 1.08 μg/ml NIP coupled to BSA at 4NIP:1BSA molar ratio in 0.05M $Na_2CO_3$, pH 9.4 overnight at 4° C. The wells of the coated plates were then washed with PBS (phosphate-buffered saline) three times and incubated with 100 μl of 3% BSA in PBS for 1 hr at 37° C. After this, the plates were ready for use in binding assays. To assay, 50 μl samples were added to the wells and incubated for 1 hr at 37° C., washed three times with PBS, incubated with 50 μl of 200 ng/ml peroxidase-labeled goat antimouse IgG(H+L) antibody in PBS for 2 hrs at 37° C. These plates were then washed with PBS and incubated with 50 μl of $H_2O_2$-ABTS substrate (Kirkegaard and Perry, Inc., Gaithersburg, Md.) at room temperature for 15–30 min. Absorbance readings were taken at 415 nm on a microtitre plate reader.

B. Purification of anti NIP-aequorin culture supernatants using immmunoaffinity chromatography NIP-agarose was prepared by coupling the N-hydroxysuccinimide ester of NIP-amino caproic acid (according to Moussebois, Van Snick, and Masson, *J.I.M.* 54:159–164 (1982)) to diamino-dipropylamine agarose at 0.55 mg of NIP-aminocaproate/ml of agarose. For purification, the transfected cells producing the antibody-photoprotein chimeric were cultured in serum free medium (HL-1, Ventrex) or, if cultured in 5% fetal calf serum, the medium was adjusted to 0.165M sodium acetate (pH 5) with a 1M solution of sodium acetate, incubated on ice for 30 min, and centrifuged for 10 min at 7000 rpm in a Sorvall/HS-4 rotor. For purification, a 1.6 ml column of NIP-agarose was equilibrated with PBS and 70–80 mls of culture supernatant loaded directly onto the column at a flow rate of 1 ml/min. The column was then washed with 10–20 vols of PBS and eluted with 1 mM NIP-aminocaproic acid in PBS. 1 ml fractions were collected. The protein level was quantitated using the BioRad protein assay. In addition, 45 μl of each fraction was analyzed by sodium dodecylsulphate-polyacrylamide gel electrophoresis (SDS-PAGE), using a 12.5% reducing gel and a 7% nonreducing gel.

The purified protein demonstrated an apparent molecular weight of 74–76 Kd on the nonreducing gel. On the reducing gel, proteins of 26 Kd, the lambda light chain, and a doublet at 50–52.5 Kd, the expression product from the plasmid p205GTi, were observed. These molecular weights agree well with the calculated molecular weight from the aequorin sequence together with the VH NP Fab fragment. These results indicate that the antibody is in the form of a Fab' fragment rather than in the form of a (Fab')$_2$ fragment.

Light producing activity of the fractions was measured on samples treated with coelenterazine in 1% 2-mercaptoethanol, 0.34 ng/ml coelenterazine, 30 mM Tris-HCl, pH 7.6, 10 mM EDTA for 3 hr at 0° C. Samples of the regenerated photoprotein (100 μl) were placed in a Berthold luminometer together with 100 μl of 30 mM $CaCl_2$, 30 mM Tris-HCl, pH 7.6 and the resultant peak light intensity was recorded (see Table 4).

TABLE 4

|  | NIP ELISA, A 415 nm. | Light, as peak intensity counts |
|---|---|---|
| Starting culture supernatant | 0.109 | 10,500 |
| Unbound material (flow thru) | 0.019 | 1,200 |

TABLE 4-continued

|  | NIP ELISA, A 415 nm. | Light, as peak intensity counts |
|---|---|---|
| NIP eluted fractions | | |
| 1 | 0.005 | 27 |
| 2 | 0.020 | 6,370 |
| 3 | 0.294 | 115,000 |
| 4 | 0.520 | 132,000 |
| 5 | 0.271 | 58,700 |
| 6 | 0.025 | 19,300 |
| 7 | 0.020 | 5,000 |

The correlation of the NIP binding activity demonstrates that a functional antigen binding site was generated in conjunction with a functional photoprotein in a single chimeric protein.

Example 7

Activation of anti-NP Aequorin Immobilized to NIP-BSA Coated Berthold Tubes

This example demonstrates the regeneration of immobilized anti-NP aequorin.

A. Methods

4-Hydroxy-3-iodo-5-nitrophenacetyl was covalently coupled to BSA (at a 1:1 molar ratio) according to Mouseebois, Van Snick and Masson, *J.I.M.* 54:159–164 (1982). NIP-BSA was diluted in 10-fold increments using 0.05M carbonate, pH 9.4. 50 μl of this mixture was incubated in Berthold tubes overnight at 4° C. The tubes were then washed with PBS and blocked with 200 μl of 3% BSA in PBS by incubation at 37° C. for 1 hr. The tubes were emptied and then incubated for 2 hr at 37° C. with 100 μl of culture supernatant containing anti-NP-aequorin. These tubes were then washed with 0.1% BSA, 0.3M HEPES, pH 7.5, and 10 mM EDTA. A wash buffer containing 1 μg/ml coelenterazine and 1% 2-mercaptoethanol (100 μl) was then added and the mixture incubated at 4° C. for 24 hr.

Light activity was assayed as described above (see Table 5).

TABLE 5

| NIP added to tube as NIP-BSA (gms) | Peak counts from Berthold |
|---|---|
| $5 \times 10^{-7}$ | 92,000 |
| $5 \times 10^{-8}$ | 104,000 |
| $5 \times 10^{-9}$ | 84,000 |
| $5 \times 10^{-10}$ | 69,000 |
| $5 \times 10^{-11}$ | 38,000 |
| $5 \times 10^{-12}$ | 28,000 |
| $5 \times 10^{-13}$ | 14,000 |
| $5 \times 10^{-15}$ | 17,000 |
| 0 | 6,650 |

B. Purified Anti-NP-Aequorin Estimation of Present Detection

Purified anti-NP-aequorin (76 μg/ml protein) was regenerated with a saturating level of coelenterazine as follows. The sample was made 0.1% BSA to stabilize the purified protein. 0.75 ng/ml anti-NP-aequorin was incubated in 1% 2-mercaptoethanol, 1 μg/ml coelenterazine, 0.3M HEPES (pH 7.5), 10 mM EDTA, and 0.1% BSA for 2 days at 4° C. Aliquots of the regenerated protein were frozen using liquid nitrogen once or twice (or not at all as a control). The samples were then assayed for light production in a Berthold Luminometer, as described above, except that the light was integrated over 10 sec (see Table 6).

| Times Frozen | Counts (over 10s integration) |
|---|---|
| 0× | 113,000 |
| 1× | 112,000 |
| 2× | 114,000 |

These results demonstrate the stability of regenerated anti-NP-aequorin on freeze thawing. The figures for the detection limit for this protein in the present regeneration and measuring system are 50 fmol at 10 fold above background counts.

C. Purified anti-NP-aequorin: Coelenterazine titration 1.1 μg/ml of purified anti-NP-aequorin protein was regenerated in 0.3M HEPES pH 7.5, 10 mM EDTA, 0.1% BSA, 1% 2-mercaptoethanol, and varying amounts of coelenterazine, for 24 hr at 4° C. These regenerated samples were assayed for light activity as described above (see Table 7).

TABLE 7

| Coelenterazine (g/ml) | Peak counts from Berthold |
|---|---|
| 4 | 47,000 |
| 3 | 42,000 |
| 2 | 41,000 |
| 1 | 43,000 |
| 0.5 | 38,000 |
| 0.25 | 34,000 |
| 0.125 | 25,000 |
| 0 | 0 |

Figure 7:
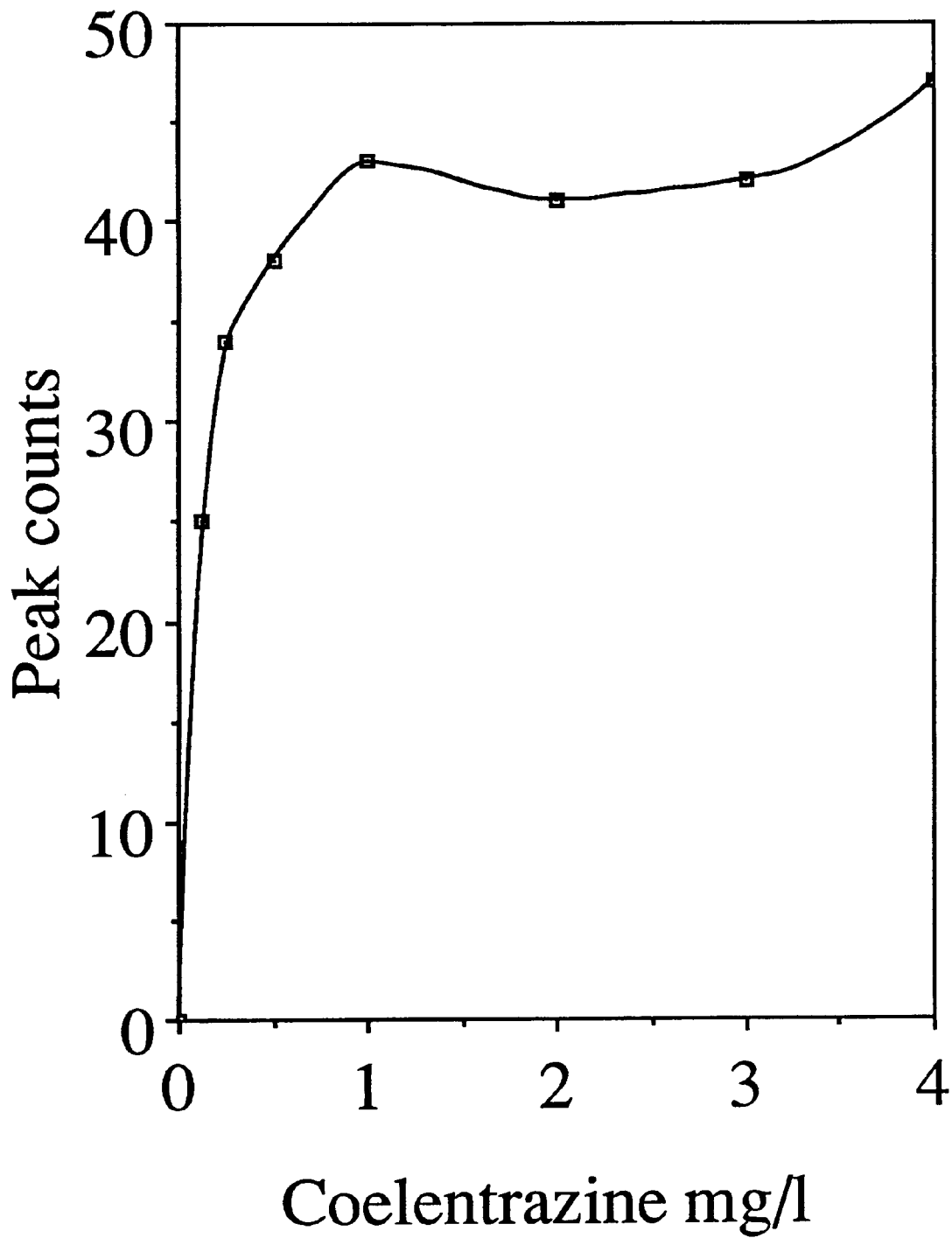
FIG. 7 depicts a graph of the amount of light activity against the concentration of coelenterazine using the aequorin-immunoglobulin chimeric protein of the invention.

A graph depicting the relationship between coelecterazine concentration and light activity is depicted in FIG. 7.

Having fully described this invention, it will be appreciated by those skilled in the art that the same can be performed within a wide range of equivalent parameters of composition, conditions, and methods of preparing such chimeric proteins without departing from the spirit or scope of the invention or any embodiment thereof.

What is claimed is:

1. A luminescent chimeric protein comprising a continuous polypeptide sequence having a first protein sequence and a second protein sequence, wherein
   (i) said continuous polypeptide sequence is composed of a linear sequence of amino acid residues covalently linked to each other through amide linkages and terminating at one end of said continuous polypeptide sequence with a terminal carboxylic acid group;
   (ii) said first protein sequence and said second protein sequence are covalently linked together through an amide linkage connecting an amino acid residue of said first protein sequence with an amino acid residue of said second protein sequence;
   (iii) said first protein sequence is a luciferase photoprotein selected from the group consisting of aequorin, obelin, mnemiopsin, and berovin;
   (iv) said second protein sequence is an amino acid sequence of an antigen-specific protein selected from the group consisting of light-chain immunoglobulin, heavy-chain immunoglobulin, avidin, streptavidin, protein A, an antigenic peptide, and an antigenically active fragment of said antigenic peptide;
   (v) said continuous polypeptide sequence exhibits both luminescent properties attributable to said luciferase photoprotein and antigen recognition properties attributable to said antigen-specific protein; and
   (vi) said continuous polypeptide sequence having been produced by protein expression using a recombinantly produced DNA gene construct.

2. The luminescent chimeric protein of claim 1, wherein said second protein sequence is an amino acid sequence of an antigen specific heavy chain immunoglobulin and said luciferase photoprotein has replaced a portion of said immunoglobulin.

3. The luminescent chimeric protein of claim 1, wherein said second protein sequence is an amino acid sequence of an antigen specific heavy chain immunoglobulin and said luciferase photoprotein has replaced the $F_c$ portion of said immunoglubulin.

4. The luminescent chimeric protein of claim 1, wherein said second protein sequence is a remnant of an amino acid sequence comprising the $V_H$ and CH-1 domains of an antigen-specific immunoglobulin.

5. The luminescent chimeric protein of claim 1 wherein said antigenic peptide and said antigenically active fragment of aid antigenic peptide are selected from the group consisting of the HIV diagnostic peptides p18, p24, gp41 and gp120, atrial natriuretic factor, the HCG diagnostic peptides, angiotensin-II, renin, insulin, glucagon, parathyroid hormone, thyroid stimulating hormone, follicle stimulating hormone, human chorionic gonadatropin, thryotropin-releasing hormone (TRH), gonadotropin-releasing hormone (GnRH), LH-releasing hormone (LHRH), corticotropin-releasing hormone (CRH), growth hormone-releasing hormone (GHRH), somatostatin (SS), growth hormone-inhibiting hormone (GHIH), thyrotropin, thyroid stimulating hormone (TSH), follicle-stimulating hormone (FSH), luteinizing hormone (LH), prolactin (PRL), growth hormone (GH), somatotropin, β-lipotropin (β-LPH), corticotropin, adenocorticotropin (ACTH), β-endorphin (β-END), α-melancycle stimulating hormone (α-MSH), leu-enkephalin (LEK), met-enkephalin (MEK), vasopressin, antidiuretic hormone (ADH), oxytocin, parathyroid hormone (PTH), parathormone, relaxin, inhibin, pancreatic polypeptide, gastrin, secretin, cholecystokinin-pancreozymin (CCK-PZ), motilin, vasoactive intestinal peptide (VIP), gastric inhibitory polypeptide (GIP), bombesin, neurotensin, substance P (SP), and hepatitis surface antigen.

* * * * *